United States Patent
Kato

(10) Patent No.: US 9,630,066 B2
(45) Date of Patent: Apr. 25, 2017

(54) GOLF CLUB SHAFT FITTING METHOD

(71) Applicants: DUNLOP SPORTS CO. LTD., Kobe-shi, Hyogo (JP); SUMITOMO RUBBER INDUSTRIES, LTD., Kobe-shi, Hyogo (JP)

(72) Inventor: Masatoshi Kato, Kobe (JP)

(73) Assignees: DUNLOP SPORTS CO. LTD., Kobe-Shi (JP); SUMITOMO RUBBER INDUSTRIES, LTD., Kobe-Shi (JP)

( * ) Notice: Subject to any disclaimer, the term of this patent is extended or adjusted under 35 U.S.C. 154(b) by 0 days.

(21) Appl. No.: 14/430,601

(22) PCT Filed: Sep. 24, 2013

(86) PCT No.: PCT/JP2013/075671
§ 371 (c)(1),
(2) Date: Mar. 24, 2015

(87) PCT Pub. No.: WO2014/050801
PCT Pub. Date: Apr. 3, 2014

(65) Prior Publication Data
US 2015/0224371 A1 Aug. 13, 2015

(30) Foreign Application Priority Data

Sep. 25, 2012 (JP) ................................. 2012-211149
Apr. 23, 2013 (JP) ................................. 2013-090791

(51) Int. Cl.
*A63B 53/00* (2015.01)
*A63B 53/02* (2015.01)
(Continued)

(52) U.S. Cl.
CPC ............ *A63B 53/02* (2013.01); *A61B 5/1122* (2013.01); *A61B 5/6895* (2013.01); *A63B 60/42* (2015.10);
(Continued)

(58) Field of Classification Search
CPC ............ A63B 2243/0029; A63B 60/42; A63B 69/3632; A63B 53/02; A63B 2220/40;
(Continued)

(56) References Cited

U.S. PATENT DOCUMENTS 6,213,888 B1 * 4/2001 Kawaguchi ........ A63B 24/0003
473/223
6,702,692 B1 3/2004 Smith
(Continued)

FOREIGN PATENT DOCUMENTS

JP 10-244023 A 9/1998
JP 2001-70482 A 3/2001
(Continued)

*Primary Examiner* — Stephen Blau
(74) *Attorney, Agent, or Firm* — Birch, Stewart, Kolasch & Birch, LLP

(57) ABSTRACT

A fitting method, of a shaft of a golf club, for selecting a shaft having a torque matching a golfer based on a swing of the golfer. The method includes the steps of obtaining measurement values from a sensor attached to a grip of the golf club and capable of measuring angular velocities about three axes when a golf ball is hit by the golf club; obtaining a predetermined index value for the angular velocities quantified from the measurement values; and selecting a shaft matching the golfer from among multiple shafts whose torques have been measured in advance, based on a relationship established through test-hitting performed in advance between the index value and a torque of a shaft.

7 Claims, 32 Drawing Sheets

(51) Int. Cl.
  *A63B 69/36* (2006.01)
  *A63B 60/42* (2015.01)
  *A61B 5/00* (2006.01)
  *A61B 5/11* (2006.01)
  *A63B 53/10* (2015.01)
  *A63B 53/14* (2015.01)

(52) U.S. Cl.
  CPC ...... *A63B 69/3632* (2013.01); *A61B 2503/10* (2013.01); *A63B 53/10* (2013.01); *A63B 53/14* (2013.01); *A63B 2220/40* (2013.01); *A63B 2220/803* (2013.01); *A63B 2220/833* (2013.01); *A63B 2225/50* (2013.01)

(58) Field of Classification Search
  CPC ........ A63B 2220/803; A63B 2220/833; A63B 53/14; A63B 2225/50; A63B 53/10; A61B 5/6895; A61B 5/1122; A61B 2503/10
  See application file for complete search history.

(56) References Cited

U.S. PATENT DOCUMENTS

| | | | | |
|---|---|---|---|---|
| 7,300,360 B2* | 11/2007 | Oyama | ........ | A63B 53/00 473/314 |
| 7,736,242 B2* | 6/2010 | Stites | ........ | A63B 69/3614 473/221 |
| 7,837,575 B2* | 11/2010 | Lee | ........ | A63B 24/0003 473/131 |
| 8,142,300 B2* | 3/2012 | Iwatsubo | ........ | A63B 24/0003 473/222 |
| 8,337,336 B2* | 12/2012 | Brekke | ........ | A63B 53/00 473/316 |
| 8,414,417 B2* | 4/2013 | Sato | ........ | A63B 53/10 473/316 |
| 8,657,707 B2* | 2/2014 | Ueda | ........ | A61B 5/6895 473/212 |
| 8,821,306 B2* | 9/2014 | Margoles | ........ | A63B 69/3623 473/131 |
| 8,827,828 B2* | 9/2014 | Brekke | ........ | A63B 53/00 473/316 |
| 8,956,238 B2* | 2/2015 | Boyd | ........ | A63B 24/0003 473/223 |
| 9,452,331 B2* | 9/2016 | Okazaki | ........ | G01B 7/001 |

FOREIGN PATENT DOCUMENTS

| | | |
|---|---|---|
| JP | 2005-21329 A | 1/2005 |
| JP | 2011-425 A | 1/2011 |

\* cited by examiner (S2)

(S1)

(S5)

(S6)

GOLF CLUB SHAFT FITTING METHOD

TECHNICAL FIELD

The present invention relates to a method for fitting shafts of golf clubs.

BACKGROUND ART

For golfers, it is an eternal theme to extend flight distance of a ball and shoot the ball in an aimed direction and angle. Therefore, it is important to use a golf club suited for one's own swing.

Selecting a golf club suited for a golfer is generally referred to as fitting. In order to effectively perform this fitting, it is necessary to take into consideration various factors such as the total weight of a golf club, the weight of a club head, and the length of the golf club. In particular, the success or failure of fitting is greatly influenced by physical properties of a shaft of a golf club.

Until now, for fitting a golf club shaft, many techniques focusing mainly on flexural rigidity of a shaft have been proposed. Yet, techniques focusing on twist rigidity (torque) of a shaft have not been much proposed.

However, during a golf swing, although it is true that the swing leads to bending of a shaft, twist motion is generated at the same time of the bending of the shaft since the center of gravity of a head is not in line with the shaft axis and since the wrist of a golfer moves during the swing. This twist motion greatly also relates to flight distance of a hit ball, directionality, and ease of swinging a golf club. In particular, directionality and ease of swinging are greatly influenced by the twist rigidity of the shaft.

Regarding the torque of the shaft, in conventional techniques, the torque has been determined empirically from a head speed upon impact and an apparent swing tempo. However, such techniques often have to depend on the experience and intuition of the person (fitter) who performs the fitting, and have a problem of the selection result being not objective and varying from person to person.

As a response thereto, a technology has been proposed in which a user is asked to swing a golf club having a sensor mounted thereto, and a golf club is designed or selected using obtained sensor data (e.g., refer to. Patent Literature 1).

In a golf club designing device/program set forth in Patent Literature 1, flex and twist rigidity of a shaft is established using the sensor data. From the sensor data, a swing response curve obtained by expressing the skill of the user as a function is calculated, and a motion of a golf club grip obtained from the swing response curve is provided as displacement data to calculate a motion of a club head.

CITATION LIST

Patent Literature

PATENT LITERATURE 1: Japanese Unexamined Patent Publication No. 2011-425

SUMMARY OF INVENTION

Technical Problem

However, with the method set forth in Patent Literature 1, since error of integration accumulates when calculating displacement from acceleration and angular velocity, and the displacement cannot be calculated with fine accuracy, a problem arises where establishing the twist rigidity becomes difficult. In addition, in the method set forth in Patent Literature 1, the method for establishing the twist rigidity is not specifically defined.

The present invention has been made in view of such a situation, and an objective of the present invention is to provide a golf club shaft fitting method enabling fitting, of a shaft having a torque that matches a swing of a golfer, to be performed objectively with fine accuracy.

Solution to Problem (1) A fitting method of a shaft of a golf club (hereinafter, also simply referred to as "fitting method") according to a first aspect of the present invention is a fitting method, of a shaft of a golf club, for selecting a shaft having a torque matching a golfer based on a swing of the golfer, the method including the steps of:

obtaining measurement values from a sensor attached to a grip of the golf club and capable of measuring angular velocities about three axes when a golf ball is hit by the golf club;

obtaining a predetermined index value for the angular velocities quantified from the measurement values; and selecting a shaft matching the golfer from among multiple shafts whose torques have been measured in advance, based on a relationship established through test-hitting performed in advance between the index value and a torque of a shaft.

In the fitting method according to the first aspect of the present invention, a grip angular velocity measured from a sensor attached to a grip is quantified to obtain an index value, and a shaft matching the golfer is selected from among multiple shafts whose torques have been measured in advance, based on the index value and a relationship established through test-hitting performed in advance between the index value and a torque of a shaft. Thus, fitting of a shaft having a torque that matches a swing of a golfer can be performed objectively with fine accuracy, and, as a result, flight distance of a hit ball, directionality, and ease of swinging can be improved.

(2) In the fitting method according to (1), the sensor is preferably attached to a grip end.

(3) In the fitting method according to (1) or (2), when x-axis is oriented in a direction along toe-heel direction of a golf club head, when y-axis is oriented in a direction in which a ball is hit, and when z-axis is oriented to match an axial direction of a shaft, the fitting method can further include the steps of:

determining address, top, and impact of a swing from the measurement values;

calculating $t_{\omega y\_max-imp}$, which is a time from when a grip angular velocity about the y-axis becomes maximum during a downswing to when the impact occurs;

calculating $\omega x_{\omega y\_max-imp}$, which is an average value of a grip angular velocity about the x-axis from when the grip angular velocity about the y-axis becomes maximum to when the impact occurs;

calculating, as the index value, a magnitude of a change amount of the grip angular velocity about the x-axis per unit of time by dividing the calculated $\omega x_{\omega y\_max-imp}$ by $t_{\omega y\_max-imp}$; and calculating the torque of the shaft from the calculated magnitude of the change amount of the grip angular velocity about the x-axis per unit of time, using an approximate formula that is prepared in advance through test-hitting and that expresses a relationship between a torque of the shaft and the magnitude of the change amount of the grip angular velocity about the x-axis.

(4) In the fitting method according to (3), as the approximate formula used for calculating the torque, one formula among multiple approximate formulae prepared in accordance with a magnitude of $\omega z\_{top}$ which is a change amount of a grip angular velocity about the z-axis around the top may be used.

(5) In the fitting method according to (4), among the multiple approximate formulae, a first approximate formula may be used when $\omega z\_{top}$ is not lower than 20 (deg/s), and a second approximate formula may be used when $\omega z\_{top}$ is lower than 20 (deg/s).

(6) In the fitting method according to (1) or (2), when x-axis is oriented in a direction along toe-heel direction of a golf club head, when y-axis is oriented in a direction in which a ball is hit, and when z-axis is oriented to match an axial direction of a shaft, the fitting method can further include the steps of:

determining address, top, and impact of a swing from the measurement values;

calculating, as the index value, $\omega z\_{top}$, which is a change amount of a grip angular velocity about the z-axis around the top; and calculating the torque of the shaft from the calculated change amount of the grip angular velocity about the z-axis, using an approximate formula that is prepared in advance through test-hitting and that expresses a relationship between a torque of the shaft and the change amount of the grip angular velocity about the z-axis.

(7) In the fitting method according to (6), as the approximate formula used for calculating the torque, one formula among multiple approximate formulae prepared in accordance with a magnitude of the change amount of the grip angular velocity about the z-axis from when the top is reached to when a grip angular velocity about the y-axis becomes maximum during a downswing may be used; and a magnitude of the change amount of the grip angular velocity about the z-axis may be a value obtained by dividing $\omega z\_{top \sim \omega y\_max}$, which is an average value of the grip angular velocity about the z-axis from when the top is reached to when the grip angular velocity about the y-axis becomes maximum during the downswing, by $t\_{top \sim \omega y\_max}$, which is a time from when the top is reached to when the grip angular velocity about the y-axis becomes maximum during the downswing.

(8) In the fitting method according to (7), among the multiple approximate formulae, a third approximate formula may be used when $\omega z\_{top \sim \omega y\_max}/t\_{top \sim \omega y\_max}$, which is a value obtained from the dividing, is not higher than $-500$ (deg/s$^2$), and a fourth approximate formula may be used when $\omega z\_{top \sim \omega y\_max}/t\_{top \sim \omega y\_max}$ is higher than $-500$ (deg/s$^2$).

(9) A fitting method according to a second aspect of the present invention is a fitting method, of a shaft of a golf club, for selecting a shaft having a twist rigidity matching a golfer based on a swing of the golfer, the method including the steps of:

obtaining measurement values from a sensor attached to a grip of the golf club and capable of measuring angular velocities about three axes when a golf ball is hit by the golf club;

obtaining a predetermined index value for the angular velocities quantified from the measurement values; and selecting a shaft matching the golfer from among multiple shafts whose twist rigidities have been measured in advance, based a relationship established through test-hitting performed in advance between the index value and a twist rigidity of a shaft wherein among multiple parts along an axial direction of a shaft, the relationship is established for each of the multiple parts, and the twist rigidities are measured at each of the multiple parts of the multiple shafts.

In the fitting method of the present invention, a grip angular velocity measured from a sensor attached to a grip is quantified to obtain an index value. Then a shaft matching the golfer is selected from among multiple shafts whose twist rigidities have been measured in advance, based on the index value and a relationship, established through test-hitting performed in advance for each of the multiple parts in the axial direction of a shaft, between the index value and a twist rigidity of the shaft. The twist rigidities are measured at each of the multiple parts of the multiple shafts. Thus, fitting of a shaft having a twist rigidity matching a swing of a golfer can be performed objectively with fine accuracy, better than a prior invention based on a twist rigidity of the whole shaft. As a result, it is possible to improve flight distance of a hit ball, directionality, and ease of swinging.

(10) In the fitting method according to (9), the multiple parts can be three parts, a front end part, a middle part, and a back end part, of the shaft.

(11) In the fitting method according to (10), the front end part may be a part located 50 to 150 mm away from a front end of the shaft, the middle part may be a part located 400 to 600 mm away from the front end of the shaft, and the back end part may be a part located 800 to 1000 mm away from the front end of the shaft.

(12) In the fitting method according to (11), the front end part may be a part located 90 mm away from the front end of the shaft, the middle part may be a part located 490 mm away from the front end of the shaft, and the back end part may be a part located 890 mm away from the front end of the shaft.

(13) In the fitting method according to (9) to (12), the sensor may be attached to a grip end.

(14) In the fitting method according to (9) to (13), when x-axis of the sensor is oriented in a direction along toe-heel direction of a golf club head, when y-axis of the sensor is oriented in a direction in which a ball is hit, and when z-axis of the sensor is oriented to match an axial direction of a shaft, the fitting method can further include the steps of:

determining address, top, and impact of a swing from the measurement values;

calculating $t\_{\omega y\_max \sim imp}$, which is a time from when a grip angular velocity about the y-axis becomes maximum during a downswing to when the impact occurs;

calculating $\omega x\_{\omega y\_max \sim imp}$, which is an average value of a grip angular velocity about the x-axis from when the grip angular velocity about the y-axis becomes maximum to when the impact occurs;

calculating, as the index value, a magnitude of a change amount of the grip angular velocity about the x-axis per unit of time by dividing the calculated $\omega x\_{\omega y\_max \sim imp}$ by $t\_{\omega y\_max \sim imp}$; and calculating the twist rigidity of each of the multiple parts from the magnitude of the calculated change amount of the grip angular velocity about the x-axis per unit of time, using an approximate formula that is prepared in advance for the multiple parts through test-hitting and that expresses a relationship between a twist rigidity of the shaft and the magnitude of the change amount of the grip angular velocity about the x-axis.

(15) In the fitting method according to (14), as the approximate formula used for calculating the twist rigidity, one formula among multiple approximate formulae prepared in accordance with a magnitude of $\omega z_{\_top}$ which is a change amount of a grip angular velocity about the z-axis around the top can be used.

(16) In the fitting method according to (15), among the multiple approximate formulae, a fifth approximate formula can be used when $\omega z_{\_top}$ is not lower than 20 (deg/s), and a sixth approximate formula can be used when $\omega z_{\_top}$ is lower than 20 (deg/s).

(17) In the fitting method according to (9) to (13), when x-axis of the sensor is oriented in a direction along toe-heel direction of a golf club head, when y-axis of the sensor is oriented in a direction in which a ball is hit, and when z-axis of the sensor is oriented to match an axial direction of a shaft, the fitting method can further include the steps of:

determining address, top, and impact of a swing from the measurement values;

calculating, as the index value, $\omega z_{top}$, which is a change amount of a grip angular velocity about the z-axis around the top; and calculating the twist rigidity of each of the multiple parts from the calculated change amount of the grip angular velocity about the z-axis, using an approximate formula that is prepared in advance for the multiple parts through test-hitting and that expresses a relationship between a twist rigidity of the shaft and the change amount of the grip angular velocity about the z-axis.

(18) In the fitting method according to (17), as the approximate formula used for calculating the twist rigidity, one formula among multiple approximate formulae prepared in accordance with a magnitude of the change amount of the grip angular velocity about the z-axis from when the top is reached to when the grip angular velocity about the y-axis becomes maximum during the downswing can be used; and the magnitude of the change amount of the grip angular velocity about the z-axis can be a value obtained by dividing $\omega z_{\_top\sim\omega y\_max}$, which is an average value of the grip angular velocity about the z-axis from when the top is reached to when the grip angular velocity about the y-axis becomes maximum during the downswing, by $t_{\_top\sim\omega y\_max}$, which is a time from when the top is reached to when the grip angular velocity about the y-axis becomes maximum during the downswing.

(19) In the fitting method according to (18), among the multiple approximate formulae, a seventh approximate formula can be used when $\omega z_{\_top\sim\omega y\_max}/t_{\_top\sim\omega y\_max}$, which is a value obtained from the dividing, is higher than −500 (deg/s$^2$), and an eighth approximate formula can be used when $\omega z_{\_top\sim\omega y\_max}/t_{\_top\sim\omega y\_max}$ is not higher than −500 (deg/s$^2$).

Advantageous Effects of Invention

With the fitting method of the present invention, fitting of a shaft having a twist rigidity or a torque matching a swing of a golfer can be performed objectively with fine accuracy, and, as a result, it is possible to improve flight distance of a hit ball, directionality, and ease of swinging.

DESCRIPTION OF EMBODIMENTS

In the following, embodiments of the fitting method of the present invention will be described in detail with reference to the accompanying drawings.

In the fitting method of the present invention, a golfer is asked to swing a golf club having attached thereto a sensor capable of measuring angular velocities in three axial directions, and a golf club shaft having a torque or a twist rigidity matching the golfer is selected based on an index value derived using a value obtained by quantifying the obtained angular velocities with a segment or a time interval of the swing (e.g., a time from when a grip angular velocity about the y-axis (direction of a wrist cock) becomes maximum to when the impact occurs).

In more detail, fitting is performed based on the torque which is the twist rigidity of the whole shaft, or respective twist rigidities at multiple parts along a shaft axial direction. As a result, accuracy of the fitting can be improved, and flight distance of a hit ball, directionality, and ease of swinging can be improved.

Figure 1:
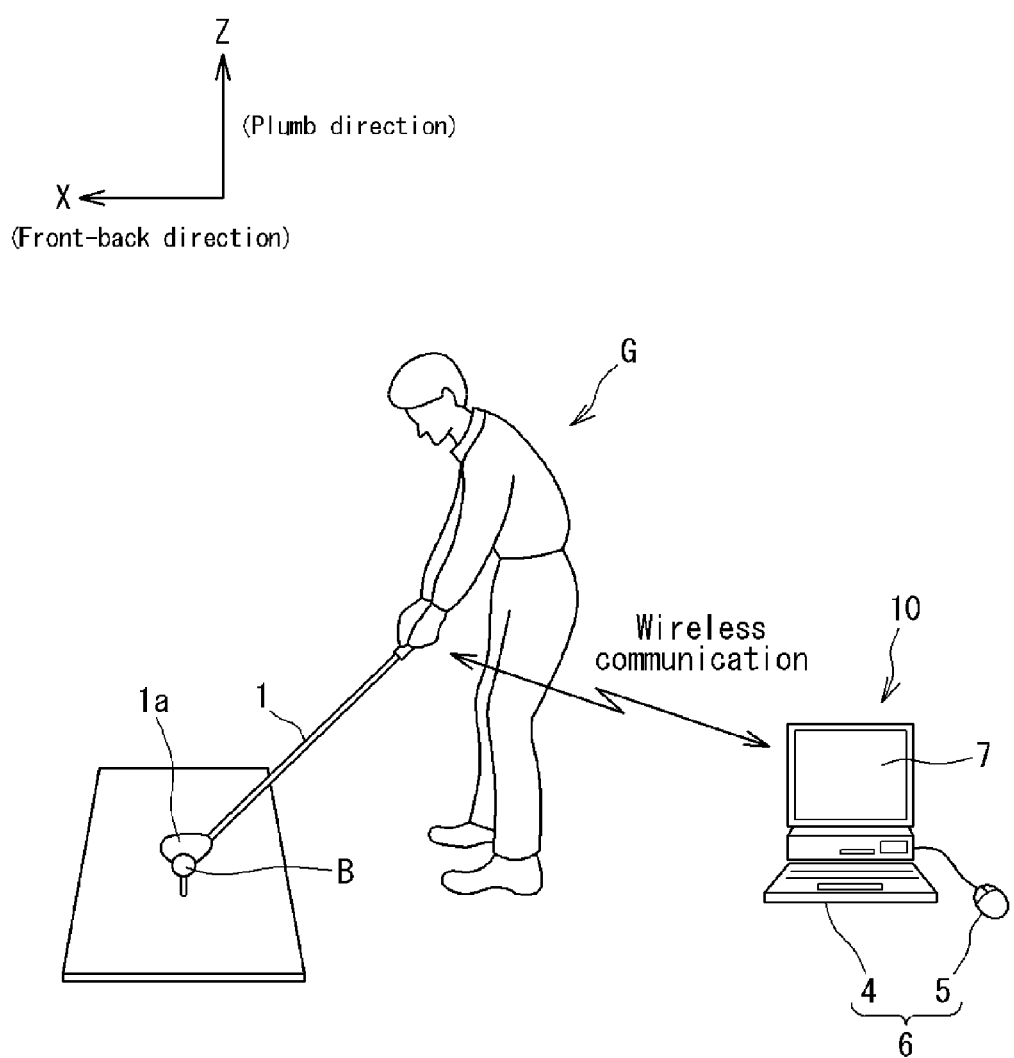
FIG. 1 is for describing a method for measuring a grip angular velocity in the present invention.
Figure 2:
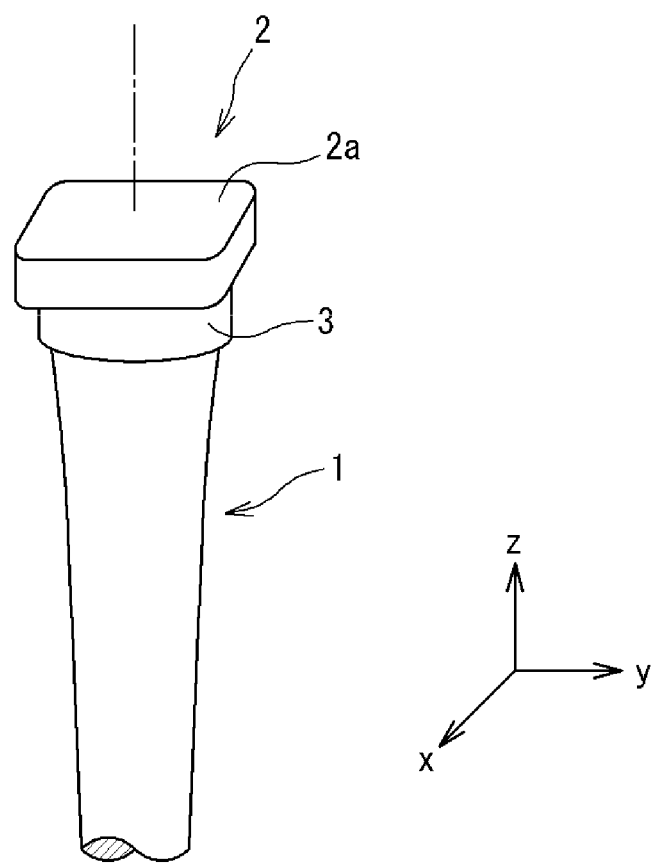
FIG. 2 is a partial expansion perspective diagram of a golf club having attached thereto a sensor.
Figure 3A:
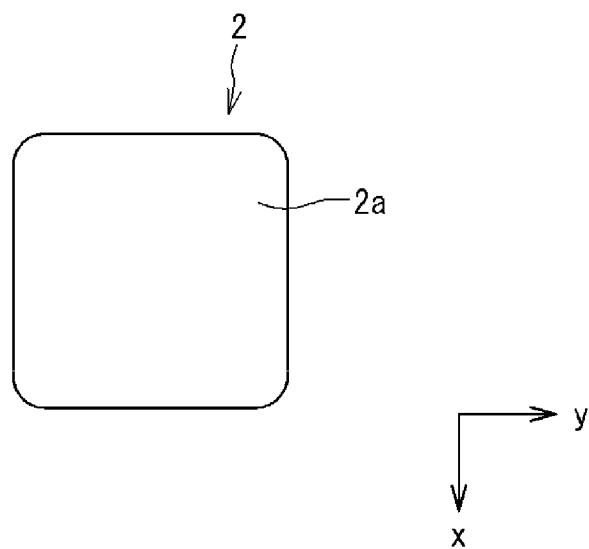
FIG. 3A is a plan view of the sensor shown in FIG. 2.
Figure 3B:
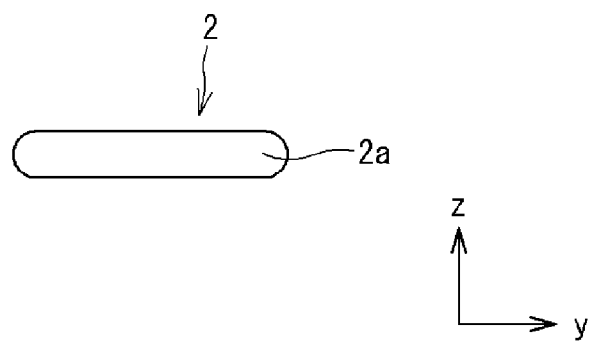
FIG. 3B is a side view of the sensor shown in FIG. 2.

In the present invention, as shown in FIG. 1, a golfer hoping for fitting of a golf club is asked to actually swing a golf club, and an "index value" specific to the golfer is calculated from the swing. At a grip end of a golf club 1, a sensor 2 capable of measuring angular velocities about three axes is attached via an adapter 3 as shown in FIGS. 2 and 3. The sensor 2 in the present embodiment includes a casing $2a$ formed from a box that has a square shape in planar view, and the casing $2a$ may be fixed to the grip end using a double-sided tape, an adhesive, a screw, or the like. In the example shown in FIG. 1, a golfer G is right handed, and is in an address state immediately before initiating a swing to hit a ball B set at a predetermined position.

It should be noted that, for the purpose of improving accuracy of fitting, if a length of a user's own club is different from a length of a golf club based on a shaft stored in a database, it is possible to select a shaft matching the user by changing a club total weight to a weight corresponding to the length of the club prepared in the database. For example, if the length of the club stored in a database is 45 inches and a length A (mm) of the club of the user is different from 45 inches (=1143 mm), the total weight of the club used for measuring a swing is changed to a weight (total weight corresponding to 45 inches) calculated from the following formula to perform the fitting.

(Total weight of club used for measurement)=($A$−1143)×0.377+(Club total weight of the user's own club)

The sensor 2 is wireless, and measured data is transmitted through wireless communication to a wireless receiver (not shown) built into a computer 10 that functions as a data analysis device. For the wireless communication, for example, standards and technologies of Bluetooth (Registered trademark) can be used.

The sensor 2 has built therein an angular velocity sensor (not shown) capable of measuring angular velocities about three axial directions (x-axial direction, y-axial direction, and z-axial direction). The sensor 2 further includes an A/D converter, a CPU, a wireless interface, a wireless antenna, and a power supply. As the power supply, for example, a button type lithium ion battery or the like can be used. The battery may be one that is rechargeable. Furthermore, the sensor 2 may also include a charging circuit for recharging a battery. Examples of the sensor 2 that can be used include WAA-010 (product name) manufactured by Wireless Technologies Inc.

It should be noted that the wireless receiver for receiving signals from the sensor 2 includes a wireless antenna, a wireless interface, a CPU, and a network interface.

The computer 10 that functions as a data analysis device includes an input section 6 including a keyboard 4 and a mouse 5, and a display section 7. Furthermore, although not diagrammatically shown, the computer 10 includes a hard disk, a memory, a CPU, and a network interface.

The sensor 2 detects angular velocities about respective axes of x-axis, y-axis, and z-axis. These angular velocities are obtained as analog signals, and these analog signals are converted into digital signals by the A/D converter built into the sensor 2. Output from the A/D converter is transmitted to the CPU and computational processes such as primary filtering are executed. Data processed in the sensor 2 in this manner is transmitted to the wireless receiver built into the computer 10 from the wireless antenna through the wireless interface.

Data transmitted from the sensor 2 is received by the wireless interface through the wireless antenna on the wireless receiver side. The received data is processed by the CPU of the computer 10.

Data sent to the computer 10 is stored in a memory resource such as the hard disk. The hard disk has stored therein a program, data, and the like required for data processing etc. The program causes the CPU to execute required data processing. The CPU is capable of executing various computation processes, and a computed result is outputted to the display section 7, or a printer or the like that is not shown.

When attaching the sensor 2 to the grip end, the relationships between measurement axes and the golf club 1 are taken into consideration. In an embodiment described later, the z-axis of the sensor 2 matches the shaft axis of the golf club 1. The x-axis of the sensor 2 is orientated so as to follow along toe-heel direction of a head $1a$ of the golf club 1. In addition, the y-axis of the sensor 2 is oriented so as to follow along a direction in which a ball is hit. By attaching the sensor 2 in such manner, it is possible to simplify computation.

In an embodiment described later, a local coordinate system is considered, and the x-axis, y-axis, and z-axis of the local coordinate system form a three-dimensional orthogonal coordinate system. In more detail, the z-axis is defined as the shaft axis of the golf club 1, and the x-axis is orientated so as to follow along the toe-heel direction of the head 1a. In addition, the y-axis is orientated so as to follow along the direction in which a ball is hit.

Thus, the z-axis of the local coordinate system matches the z-axis of the sensor 2, and the y-axis of the local coordinate system matches the y-axis of the sensor 2. In addition, the x-axis of the local coordinate system matches the x-axis of the sensor 2.

With the sensor 2, a plurality of chronologically successive data points can be obtained. The number of data points per unit of time depends on sampling frequency.

FIGS. 4 to 7 are for describing a swing by a golfer from the address to the finish. Although the swing includes the follow-through after the impact, in the present invention, focus has been placed on characteristics of the swing from the address to the impact.

Figure 4:
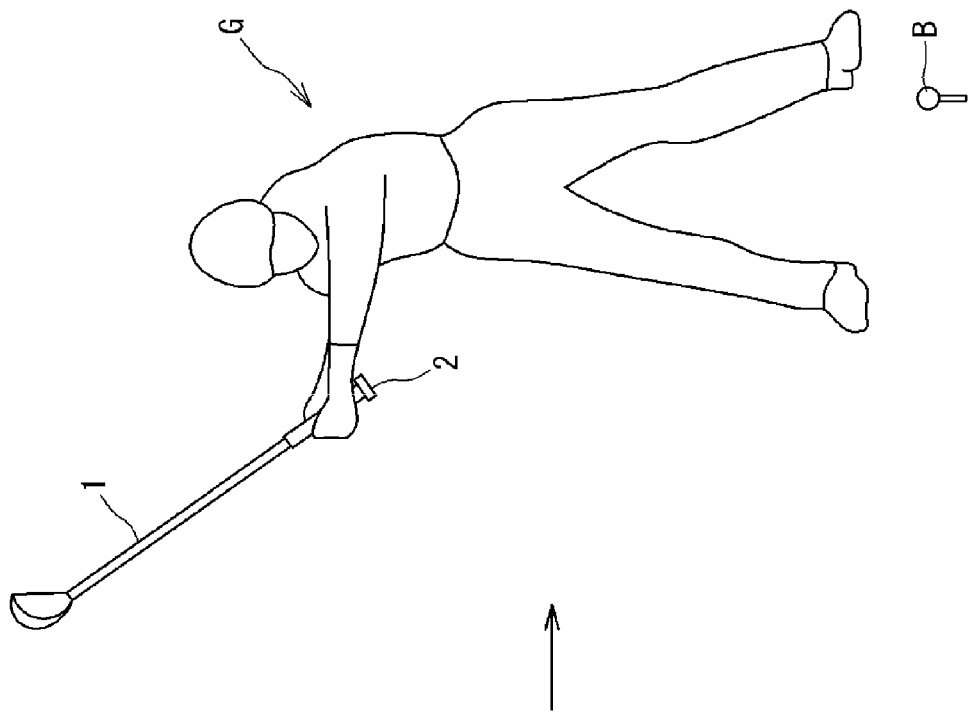
FIG. 4 shows the address and backswing in a swing.
Figure 4:
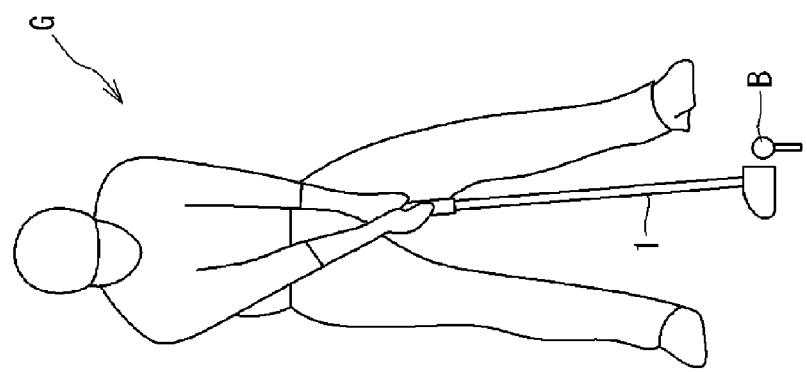
Figure 5:
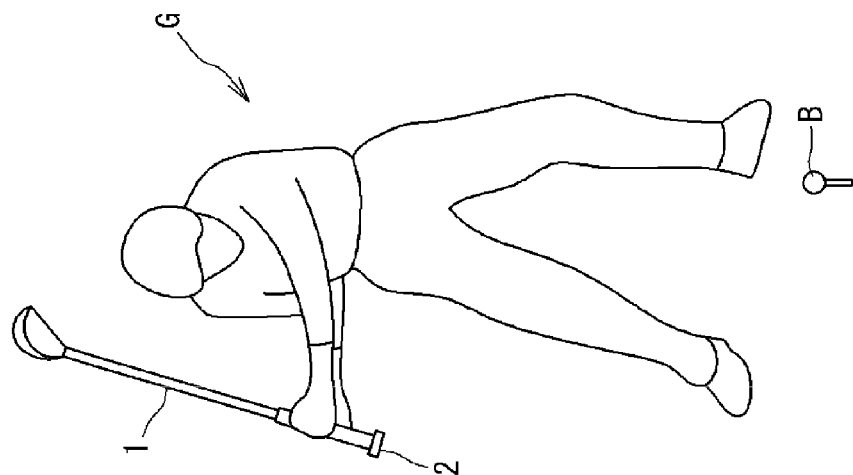
FIG. 5 shows the top and downswing in a swing.
Figure 5:
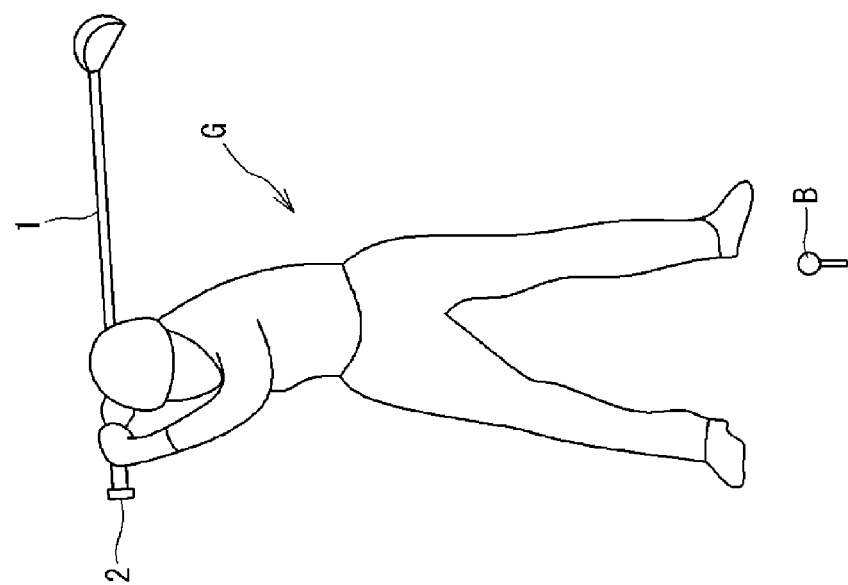
Figure 6:
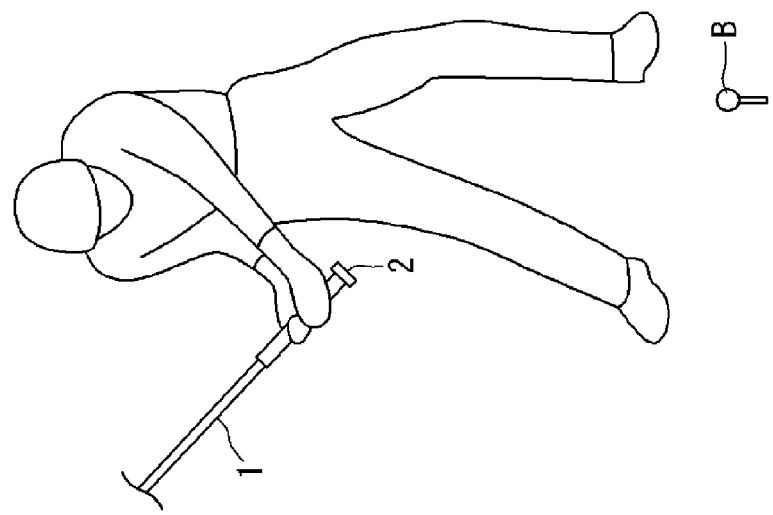
FIG. 6 shows the downswing and impact in a swing.
Figure 6:
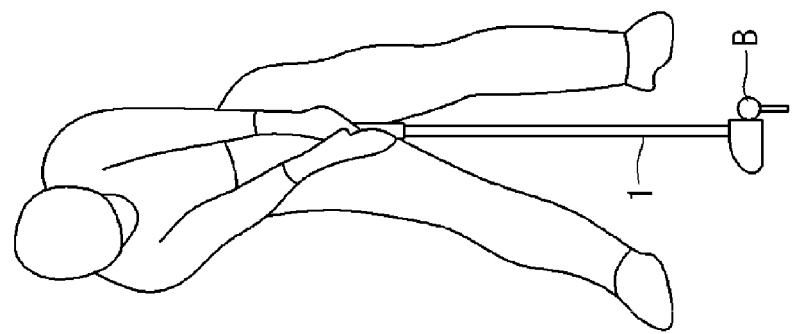
Figure 7:
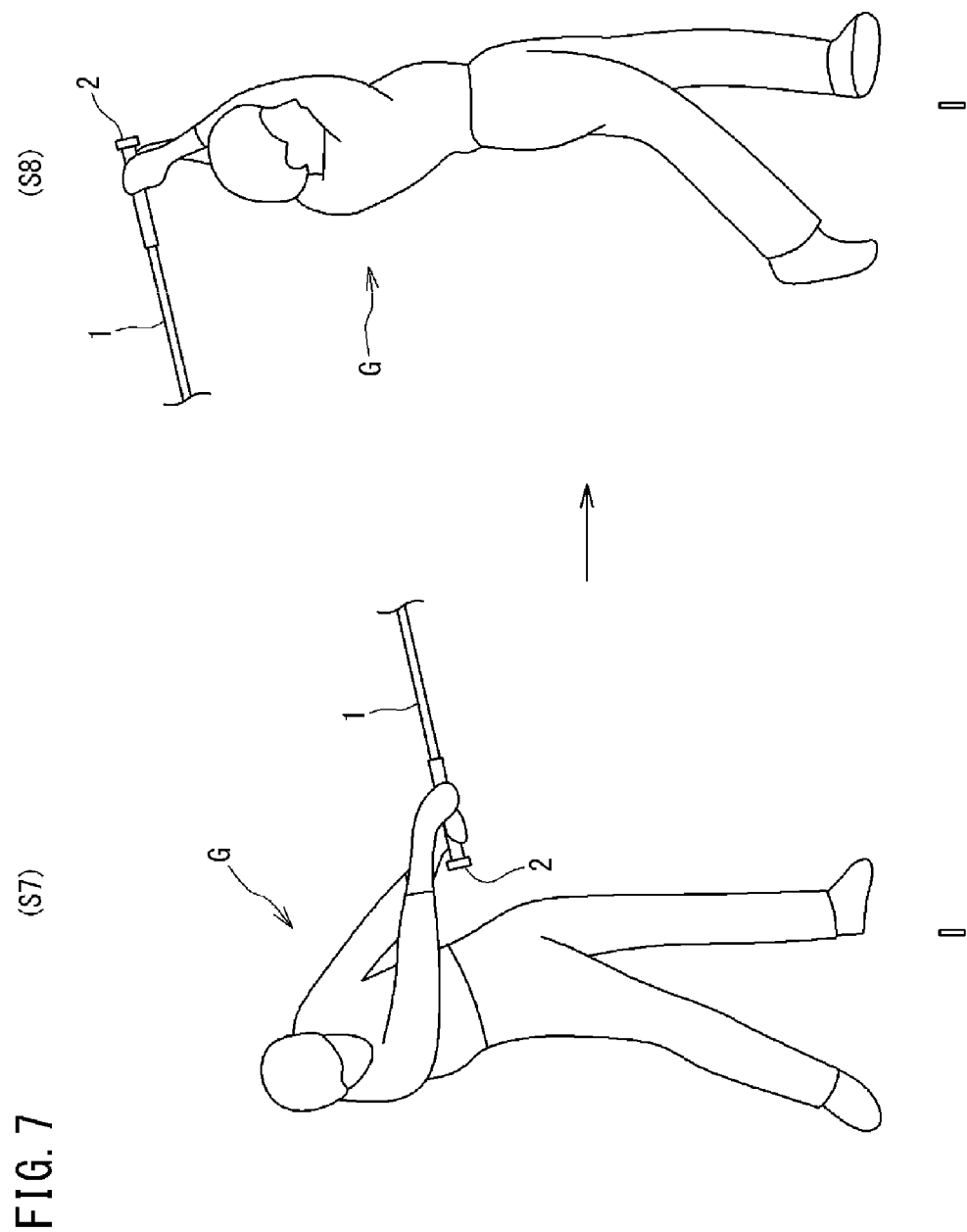
FIG. 7 shows the follow-through and finish in a swing.

FIGS. 4 to 7 are views of a golfer from the front. The beginning of a swing is referred to as the address, and the end of a swing is referred to as the finish. The swing proceeds in a sequence of (S1), (S2), (S3), (S4), (S5), (S6), (S7), and (S8). In FIG. 4, (S1) is the address, and (S2) is the backswing. In FIG. 5, (S3) is the top (top of swing). Ordinarily, the movement velocity of the head during a swing is lowest at the top. In FIG. 5, (S4) is the downswing. Although (S5) in FIG. 6 is also the downswing, it is a more advanced state of the downswing than (S4) in FIG. 5. In FIG. 6, (S6) is the impact, which is the moment when the head 1a of the golf club 1 and the ball B collide. In FIG. 7, (S7) is the follow-through, and (S8) is the finish. With the finish, the swing ends.

Figure 8:
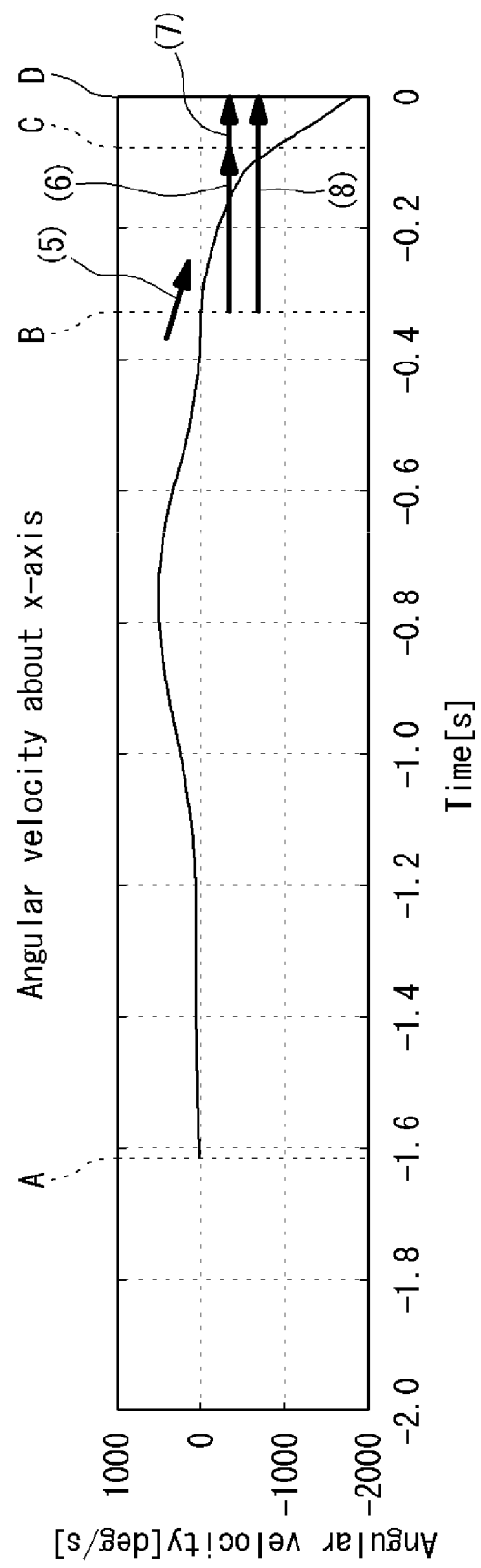
FIG. 8 shows one example of a change in angular velocity about x-axial direction in accordance with elapsed time during a swing.
Figure 9:
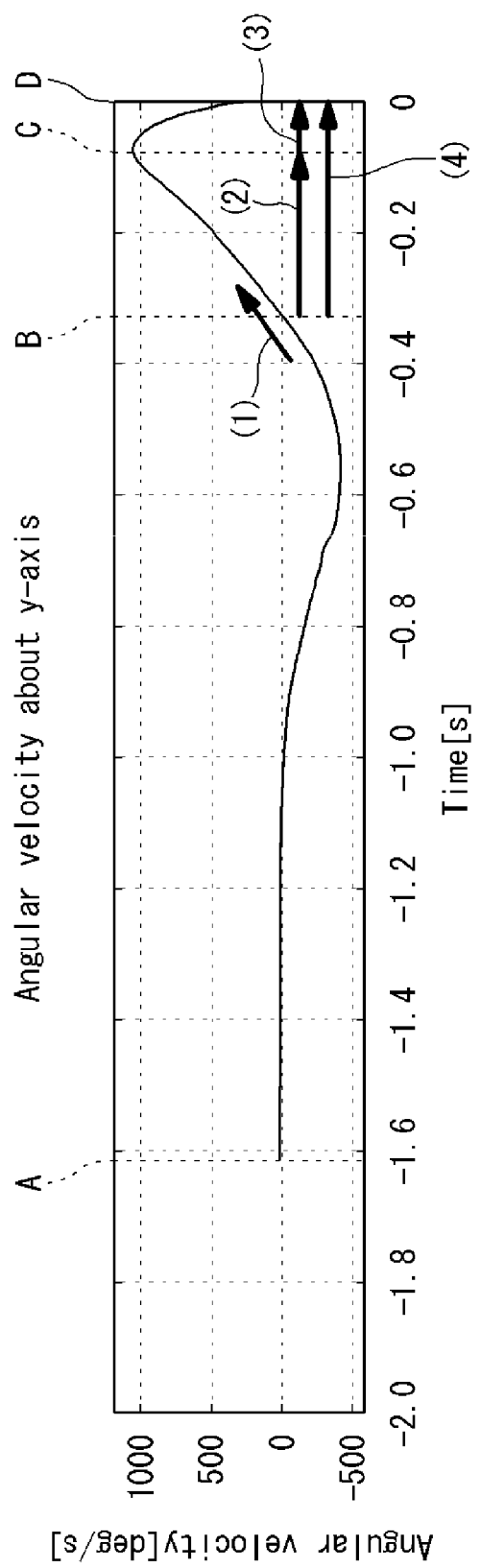
FIG. 9 shows one example of a change in angular velocity about y-axial direction in accordance with elapsed time during a swing.
Figure 10:
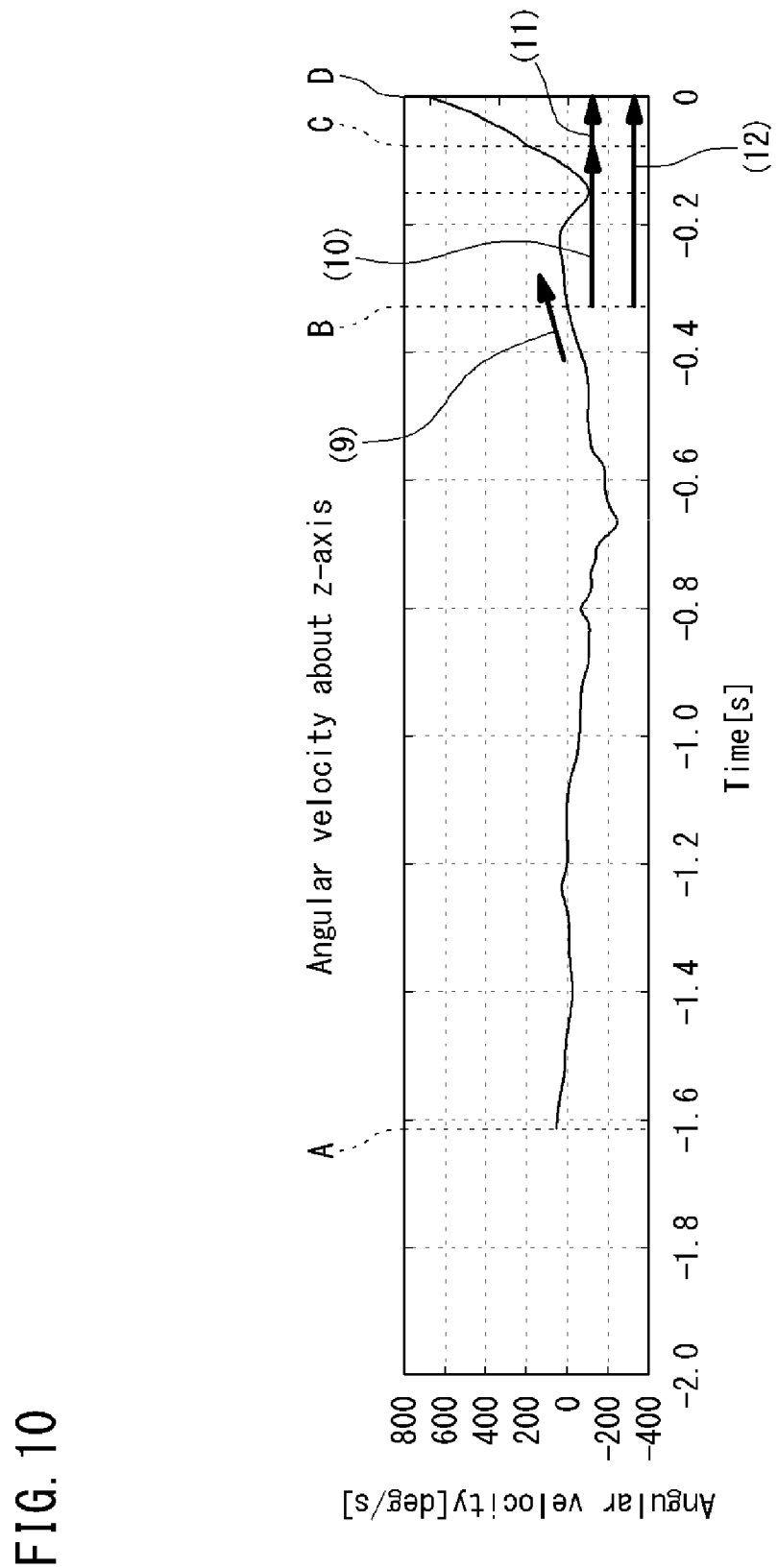
FIG. 10 shows one example of a change in angular velocity about z-axial direction in accordance with elapsed time during a swing.

Regarding a certain swing: FIG. 8 shows a relationship between time (s) from the address to the impact and an angular velocity ωx (deg/s) about the x-axis; FIG. 9 shows a relationship between the same time (s) from the address to the impact and an angular velocity ωy (deg/s) about the y-axis; and FIG. 10 shows a relationship between the same time (s) from the address to the impact and an angular velocity ωz (deg/s) about the z-axis. In FIGS. 8 to 10, time points A to D respectively represent a start point of a swing, the top of the swing, a time point at which the grip angular velocity about the y-axis (wrist cock) becomes maximum, and the impact of the swing. In an embodiment described later, as shown in FIGS. 8 to 10, predetermined index values are set in accordance with the elapsed time of the swing, and each of the index values is obtained by quantifying the grip angular velocity. For example, a quantitative value (7) in FIG. 8 is $\omega x\_{\omega y\_max\sim imp}$, which is an average value of the grip angular velocity about the x-axis from when the grip angular velocity about the y-axis becomes maximum to when the impact occurs during the downswing. In addition, a quantitative value (9) in FIG. 10 is $\omega z\_{top}$, which is a change amount of the grip angular velocity about the z-axis around the top. Furthermore, a quantitative value (10) in FIG. 10 is $\omega z\_{top\sim\omega y\_max}$, which is an average value of the grip angular velocity about the z-axis from when the top is reached to when the grip angular velocity about the y-axis becomes maximum during the downswing.

[First Embodiment]

In the present embodiment, fitting is performed based on the torque, which is the twist rigidity of the whole shaft.

Figure 11:
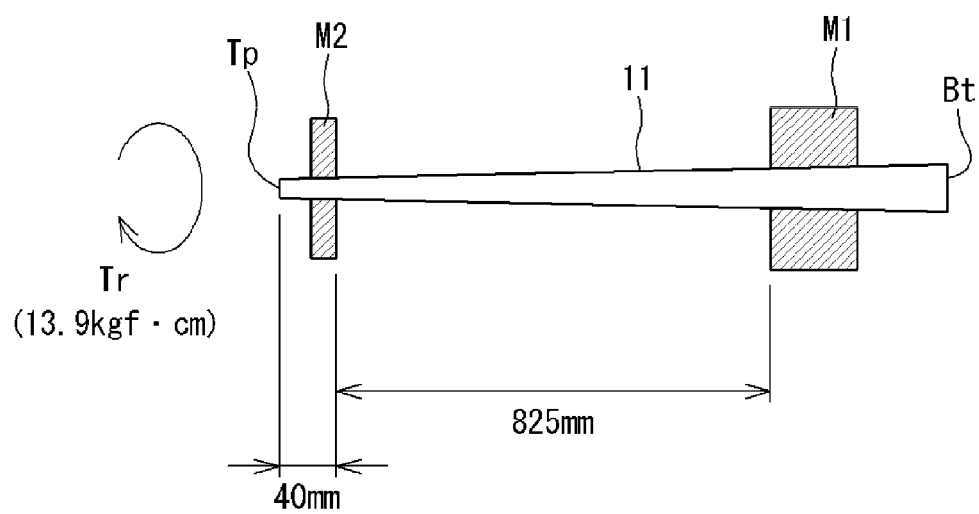
FIG. 11 is for describing a method for measuring a torque of a shaft.

FIG. 11 is for describing a method for measuring the torque of a shaft 11 of the golf club 1. In this measuring method, a rear end part of the shaft 11 is unrotatably fixed by a jig M1 and a front end part of the shaft 11 is held by a jig M2 to apply a torque Tr of 13.9 kgf·cm on a position located 40 mm away from a tip end Tp. A torsion angle (degrees) of the shaft 11 at this torque applying position is defined as a shaft torque value. A rotational velocity of the jig M2 when applying the torque Tr is set equal to or lower than 130 deg/min., and a length in the axial direction between the jig M1 and the jig M2 is set to 825 mm. Furthermore, when the shaft 11 deforms due to being held by the jig M1 or the jig M2, the measurement is performed after the inside of the shaft 11 is filled with a core material or the like.

[Index Value]

In the present embodiment, among the above described various stages of the swing, focus is placed on the grip angular velocity from around the top to the impact during a downswing, and the angular velocity is subdivided and quantified in accordance with the elapsed time. Then, a shaft of a golf club is selected based on an index value calculated using the quantified value (quantitative value), and a relationship, obtained in advance through test-hitting, between the index value and the torque that matches a golfer. It should be noted that, in the present specification, "around the top" refers to a time interval including a predetermined time immediately before the top and a predetermined time immediately after the top, and more specifically, refers to a time interval of, for example, 100 ms between −50 ms from the top and +50 ms from the top.

The "index value" in the present embodiment is a value calculated by quantifying the grip angular velocity, and is a value that is recognized to correlate with the torque matching a golfer. Examples thereof include those shown in the following. It should be noted that a match with a golfer includes a case where evaluation is performed objectively based on such as standard deviation σ of scattering to the left and right of a hit ball for directionality of a hit ball, and a case where evaluation is performed through a sensory test (interview survey) on a golfer for the ease of swinging a club.

(1) Index Value (A): Magnitude of Change Amount of Grip Angular Velocity about x-Axis Per Unit of Time, from when Grip Angular Velocity about y-Axis Becomes Maximum to when Impact Occurs This index value (A) is a value that is recognized to correlate with the torque matching a golfer particularly in terms of improving directionality of a hit ball. Directionality of a hit ball is determined by the direction of a club face immediately before impact, and a club face angle is highly correlated with the change amount of the grip angular velocity about the x-axis immediately before the impact. Thus, when the change amount of the angular velocity about the x-axis immediately before the impact is higher, the club head is accelerated more rapidly and the club face direction easily becomes open or is easily upset at the moment of the impact. When a shaft having a low torque is selected for such a golfer, since variation of the club face angle becomes small and opening of the club face is suppressed, directionality of a hit ball improves. Similarly in an opposite case, when the change amount of the angular velocity about the x-axis immediately before the impact is low, the club face cannot be actively set open and the ball is easily yanked, resulting in deterioration of directionality of a hit ball. In addition, when the club face cannot be set open, the flight distance becomes small since the loft angle upon impact becomes insufficient. When a shaft having a high torque is selected for such a golfer, the club face is set open properly, directionality of a hit ball improves, and a larger flight distance is obtained since a proper loft angle is obtained.

The index value (A) is calculated as described next.

First, from the waveform of the grip angular velocity ωy about the y-axis, $t_{\omega y\_max\sim imp}$, which is a time (t1) from when the grip angular velocity about the y-axis becomes maximum during a downswing to when the impact occurs, is calculated.

Next, $\omega x_{\omega y\_max\sim imp}$, which is an average value (m1) of the grip angular velocity about the x-axis from when the grip angular velocity about the y-axis becomes maximum during a downswing to when the impact occurs, is calculated.

Then, by dividing the average value (m1) by the time (t1), the index value (A), which is the magnitude of the change amount of the grip angular velocity about the x-axis per unit of time from when the grip angular velocity about the y-axis becomes maximum to when the impact occurs, is obtained.

$$\text{Index value }(A) = \omega x_{\omega y\_max\sim imp}/t_{\omega y\_max\sim imp}$$

The torque is calculated based on the index value (A) calculated in such manner, and a relationship, obtained in advance through test-hitting, between the index value (A) and the torque matching a golfer regarding directionality of a hit ball, more specifically, based on an approximate formula representing the relationship of the two.

For example, when $\omega x_{\omega y\_max\sim imp}/t_{\omega y\_max\sim imp}$ is represented as x, the following formula (1) representing a regression line obtained through least squares method can be used as the approximate formula.

$$\text{Torque (deg)} = -0.0000547x + 5.17 \quad (1)$$

(2) Index Value (B): Change Amount of Grip Angular Velocity about z-Axis Around the Top Although the torque can be calculated using the approximate formula (e.g., formula (1) described above) representing the relationship between the index value (A) and the torque matching a golfer regarding directionality of a hit ball, it is possible to, for further improving directionality, stratify the relationship between the index value (A) and the torque by using this index value (B).

The change amount of the grip angular velocity about the z-axis around the top, i.e., $\omega z_{\_top}$, is positive in a direction in which a club face becomes closed. With a golfer whose $\omega z_{\_top}$ is positive, a golf club is swung down while having the right hand covering thereover at the top. Since the covering by the right hand causes the club face to close easily, when a shaft having a low torque is used, the club face does not open during the downswing and the ball is yanked upon impact, or the wrist is used too extensively to cause the club face to open, resulting in deteriorated directionality due to having some balls that cannot be caught or having some sliced balls. Thus, a golfer whose ($\omega z_{\_top}$ is positive preferably selects a shaft having a high torque.

On the other hand, with a golfer whose $\omega z_{\_top}$ is negative or low, since the club face moves in a direction to open, if the impact occurs with the club face being open or a shaft having a high torque is used, the wrist becomes closed to avoid the club face from being too open during the downswing, and yanking or a hook ball occurs easily. Thus, a golfer whose $\omega z_{\_top}$ is negative or low preferably selects a shaft having a low torque.

As described above, preferably, the relationship between the torque and the index value (A) is stratified in accordance with the magnitude of $\omega z_{\_top}$, and one suitable approximate formula among multiple approximate formulae prepared in advance is used.

For example, when $\omega x_{\omega y\_max\sim imp}/t_{\omega y\_max\sim imp}$ is represented as x, the following formula (2) representing a regression line obtained through least squares method can be used as the approximate formula (first approximate formula) in cases where $\omega z_{\_top}$ is not lower than 20 (deg), and the following formula (3) representing the same can be used as the approximate formula (second approximate formula) in cases where $\omega z_{\_top}$ is lower than 20 (deg).

$$\text{Torque (deg)} = -0.0000571x + 5.45 \quad (2)$$

$$\text{Torque (deg)} = -0.0000571x + 4.70 \quad (3)$$

Although the index value (B) can be used for stratification when calculating the torque using the index value (A), the index value (B) itself is a value that is recognized to correlate with the torque matching a golfer particularly in terms of improving the ease of swinging. Thus, the torque can also be calculated by using the index value (B).

The ease of swinging a golf club refers to the ease of matching the timing, and it is thought that a swing is sensed as being easy when the swing and torsion of the shaft synchronize. In the present invention, when various tests (test-hitting) were performed, and the ease of swinging was scored using questionnaires to examine its correlation with swing index values, it was revealed that the ease of swinging a golf club highly correlates with $\omega z_{\_top}$, which is the change amount of the grip angular velocity about the z-axis around the top. Thus, it is thought that a phenomenon similar to that observed in the stratification of fitting focusing on directionality described above is occurring, and the index value (B) is linked to the timing of the impact.

Thus, the torque can be calculated based on the index value (B) and the relationship, obtained in advance through test-hitting, between the index value (B) and the torque matching a golfer regarding the ease of swinging a golf club, more specifically, based on the approximate formula representing the relationship of the two.

For example, when $\omega z_{\_top}$ is represented as x, the following formula (4) representing a regression line obtained through least squares method can be used as the approximate formula.

$$\text{Torque (deg)} = 0.00939x + 3.38 \quad (4)$$

(3) Index Value (C): Magnitude of Change Amount of Grip Angular Velocity about z-Axis from when the Top is Reached to when Grip Angular Velocity about y-Axis Becomes Maximum During Downswing Although the torque can be calculated using the approximate formula (e.g., formula (4) described above) representing the relationship between the index value (B) and the torque matching a golfer regarding the ease of swinging a golf club, it is possible to, for further improving the ease of swinging, stratify the relationship between the index value (B) and the torque by using this index value (C).

The index value (C) can be calculated in the following manner.

First, from the waveform of the grip angular velocity ωy in the y-axial direction, $t_{\_top\sim\omega y\_max}$, which is a time (t2) from when the top is reached to when the grip angular velocity about the y-axis becomes maximum during a downswing, is calculated.

Next, $\omega z_{\_top\sim\omega y\_max}$, which is an average value (m2) of the grip angular velocity about the z-axis from when the top is reached to when the grip angular velocity about the y-axis becomes maximum during a downswing, is calculated.

Then, by dividing the average value (m2) by the time (t2), the index value (C), which is the magnitude of the change amount of the grip angular velocity about the z-axis from when the top is reached to when the grip angular velocity about the y-axis becomes maximum during a downswing, is obtained.

$$\text{Index value }(C) = \omega z_{\_top\sim\omega y\_max}/t_{\_top\sim\omega y\_max}$$

With a golfer whose index value (C) is high, the change amount of shaft torsion (in a club face opening direction) at the beginning of a downswing is high. Particularly when the index value (C) is negative and an absolute value thereof is high, the club face is actively set open. Thus, when a shaft having a high torque is used, it becomes difficult to match the timing and the feeling deteriorates since the club face is set too open or varies too much. Therefore, a golfer whose index value (C) is high preferably selects a shaft having a low torque.

On the other hand, since a golfer whose index value (C) is low, i.e., whose change amount of the angular velocity is low, does not actively open or close the club face; when a shaft having a low torque is used, rotation of the club face does not occur and the shaft may present a hard sensation. Therefore, a golfer whose index value (C) is low preferably selects a shaft having a high torque.

As described above, preferably, the relationship between the torque and the index value (B) is stratified in accordance with the magnitude of $\omega z\_{top\text{-}\omega y\_max}/t\_{top\text{-}\omega y\_max}$, and one suitable approximate formula among multiple approximate formulae prepared in advance is used.

For example, when $\omega z\_{top}$ is represented as x, the following formula (5) representing a regression line obtained through least squares method can be used as the approximate formula (third approximate formula) in cases where $\omega z\_{top\text{-}\omega y\_max}/t\_{top\text{-}\omega y\_max}$ is not higher than −500 (deg), and the following formula (6) representing the same can be used as the approximate formula (fourth approximate formula) in cases where $\omega z\_{top\text{-}\omega y\_max}/t\_{top\text{-}\omega y\_max}$ is higher than −500 (deg).

$$\text{Torque (deg)} = 0.00991x + 3.50 \tag{5}$$

$$\text{Torque (deg)} = 0.00991x + 2.90 \tag{6}$$

[How to Obtain Approximate Formula]

For example, the approximate formula can be obtained as described in the following.

As testers, twenty right-handed males having a handicap of 2 to 20 were gathered. As a golf club, SRIXON Z-TX2 (club length: 45.0 inches, loft angle: 9.5 degrees) manufactured by Dunlop Sports Co., Ltd., was used. As shown in Table 1, as shafts, 3 types of flexes (corresponding to X/S/R) were prepared, and, for each of the flexes, 5 types of torques of 3.0, 3.5, 4.0, 4.5, and 5.0 were prepared. A head and a shaft were structured to be detachable from each other, and each of the testers performed test-hitting consistently using the same head during the test. A tester with a high trajectory was asked to use a head with a more upright loft, and a tester with a low trajectory was asked to use a head with a more laid loft.

TABLE 1

| Flex | Forward Flex [mm] | Torque [deg] |
|---|---|---|
| X | 85 | 3.0 |
|   |   | 3.5 |
|   |   | 4.0 |
|   |   | 4.5 |
|   |   | 5.0 |
| S | 100 | 3.0 |
|   |   | 3.5 |
|   |   | 4.0 |
|   |   | 4.5 |
|   |   | 5.0 |
| R | 110 | 3.0 |
|   |   | 3.5 |
|   |   | 4.0 |
|   |   | 4.5 |
|   |   | 5.0 |

The grip angular velocity was measured using the measuring method described with reference to FIG. 1. SRIXON Z-STAR XV manufactured by Dunlop Sports Co., Ltd., was used as a ball, and the test-hitting was performed using 5 balls for each club (shaft), resulting in a total of 25 balls. However, an obvious miss-shot was excluded, and a redo of the test-hit was performed.

The directionality of a hit ball was evaluated based on standard deviation a of the scattering to the left and right, and a shaft whose a was the smallest was evaluated as a shaft with fine directionality. In addition, the ease of swinging was determined by having each of the testers test-hit 5 balls each for the 5 types of shafts, and then performing an interview survey on each of the testers regarding a shaft that provided the best ease of swinging. The results are shown in Table 2.

TABLE 2

| Used shaft | Head speed | Shaft providing finest directionality Torque = | | | | | Shaft providing best ease of swinging Torque = | | | | |
|---|---|---|---|---|---|---|---|---|---|---|---|
| | | 3.0 | 3.5 | 4.0 | 4.5 | 5.0 | 3.0 | 3.5 | 4.0 | 4.5 | 5.0 |
| A | X | 50.2 | ○ |   |   |   |   | ○ |   |   |   |   |
| B | X | 48.8 | ○ |   |   |   |   |   | ○ |   |   |   |
| C | X | 47.3 | ○ |   |   |   |   |   | ○ |   |   |   |
| D | X | 47.1 |   | ○ |   |   |   |   | ○ |   |   |   |
| E | X | 45.1 | ○ |   |   |   |   |   | ○ |   |   |   |
| F | S | 45.7 | ○ |   |   |   |   |   | ○ |   |   |   |
| G | S | 45.0 |   | ○ |   |   |   |   |   | ○ |   |   |
| H | S | 44.4 |   |   | ○ |   |   |   |   |   | ○ |   |
| I | S | 44.1 | ○ |   |   |   |   |   | ○ |   |   |   |
| J | S | 43.2 |   |   | ○ |   |   |   | ○ |   |   |   |
| K | S | 42.0 |   |   | ○ |   |   |   | ○ |   |   |   |
| L | S | 41.9 |   |   |   | ○ |   |   |   |   | ○ |   |
| M | S | 41.8 |   |   | ○ |   |   |   |   |   |   | ○ |
| N | S | 41.4 | ○ |   |   |   |   |   | ○ |   |   |   |
| O | S | 40.3 |   |   |   | ○ |   |   |   |   |   | ○ |
| P | R | 39.2 |   |   |   | ○ |   |   |   |   | ○ |   |
| Q | R | 39.1 | ○ |   |   |   |   |   |   |   |   | ○ |

TABLE 2-continued

Shaft providing finest directionality | Shaft providing best ease of swinging

| Used shaft | Head speed | Torque = 3.0 | 3.5 | 4.0 | 4.5 | 5.0 | Torque = 3.0 | 3.5 | 4.0 | 4.5 | 5.0 |
|---|---|---|---|---|---|---|---|---|---|---|---|
| R | R | 38.9 | | | ○ | | | | | ○ | |
| S | R | 38.5 | | | | ○ | | | | ○ | | |
| T | R | 37.8 | | ○ | | | | | | | ○ | |

By using data of the measured grip angular velocity, the above described index values (A) to (C) were calculated. The calculation result and the torque of the shaft providing the finest directionality evaluated using the standard deviation σ of the scattering to the left and right of the hit ball are shown in Tables 3 and 4. In addition, the same calculation result, and the torque of the shaft providing the best ease of swinging determined by the interview survey are shown in Tables 5 and 6. Tables 3 to 6 respectively correspond to FIGS. 12 to 15.

TABLE 3

| Tester | Flex | Shaft torque providing finest directionality | Index value (A) $\omega x\_(\omega y\_max\sim imp)/t\_(\omega y\_max\sim imp)$ | Index value (B) $\omega z\_top$ |
|---|---|---|---|---|
| A | X | 3.0 | 45008.0 | 8.8 |
| B | X | 3.0 | 28774.2 | −45.8 |
| C | X | 3.0 | 42052.4 | 39.1 |
| D | X | 3.5 | 30005.6 | 85.1 |
| E | X | 3.0 | 25271.3 | −64.2 |
| F | S | 3.0 | 27499.6 | −1.2 |
| G | S | 3.5 | 29293.9 | 61.3 |
| H | S | 4.0 | 25570.2 | 51.1 |
| I | S | 3.5 | 34502.8 | 100.0 |
| J | S | 4.0 | 20856.1 | 49.2 |
| K | S | 4.0 | 20770.2 | 66.2 |
| L | S | 4.5 | 22593.5 | 117.0 |
| M | S | 4.0 | 22593.5 | 118.0 |
| N | S | 3.5 | 20315.1 | 14.2 |
| O | S | 4.5 | 23287.4 | 99.6 |
| P | R | 4.5 | 20023.1 | 94.0 |
| Q | R | 3.5 | 20697.1 | 94.0 |
| R | R | 4.5 | 17245.6 | 84.6 |
| S | R | 5.0 | 14793.0 | 33.5 |
| T | R | 4.0 | 16087.4 | 132.5 |

TABLE 4

| Tester | Flex | Shaft torque providing finest directionality | Index value (A) $\omega x\_(\omega y\_max\sim imp)/t\_(\omega y\_max\sim imp)$ | Index value (B) $\omega z\_top$ |
|---|---|---|---|---|
| C | X | 3.0 | 42052.4 | 39.1 |
| D | X | 3.5 | 30005.6 | 85.1 |
| G | S | 3.5 | 29293.9 | 61.3 |
| H | S | 4.0 | 25570.2 | 51.1 |
| I | S | 3.5 | 34502.8 | 100.0 |
| J | S | 4.0 | 20856.1 | 49.2 |
| K | S | 4.0 | 20770.2 | 66.2 |
| L | S | 4.5 | 22593.5 | 117.0 |
| M | S | 4.0 | 22593.5 | 118.0 |
| O | S | 4.5 | 23287.4 | 99.6 |
| P | R | 4.5 | 20023.1 | 94.0 |
| Q | R | 3.5 | 20697.1 | 94.0 |
| R | R | 4.5 | 17245.6 | 84.6 |
| S | R | 5.0 | 14793.0 | 33.5 |
| T | R | 4.0 | 16087.4 | 132.5 |
| A | X | 3.0 | 45008.0 | 8.8 |
| B | X | 3.0 | 28774.2 | −45.8 |
| E | X | 3.0 | 25271.3 | −64.2 |
| F | S | 3.0 | 27499.6 | −1.2 |
| N | S | 3.5 | 20315.1 | 14.2 |

TABLE 5

| Tester | Flex | Shaft torque providing best ease of swinging | Index value (B) $\omega z\_top$ | Index value (C) $\omega z\_top\sim\omega y\_max/t\_top\sim\omega y\_max$ |
|---|---|---|---|---|
| A | X | 3.5 | 8.8 | −447.4 |
| B | X | 3.0 | −45.8 | 10.1 |
| C | X | 3.0 | 39.1 | −609.1 |
| D | X | 3.5 | 85.1 | −909.8 |
| E | X | 3.0 | −64.2 | −71.0 |
| F | S | 3.5 | −1.2 | −354.9 |
| G | S | 4.0 | 61.3 | −591.3 |
| H | S | 4.5 | 51.1 | −364.0 |
| I | S | 3.5 | 100.0 | −571.0 |
| J | S | 3.5 | 49.2 | 120.0 |
| K | S | 3.5 | 66.2 | −338.7 |
| L | S | 4.5 | 117.0 | −298.3 |
| M | S | 5.0 | 118.0 | −245.0 |
| N | S | 3.5 | 14.2 | −275.2 |
| O | S | 5.0 | 99.6 | −22.1 |
| P | R | 4.5 | 94.0 | 186.1 |
| Q | R | 4.5 | 94.0 | 243.6 |
| R | R | 4.5 | 84.6 | −432.2 |
| S | R | 4.0 | 33.5 | −488.4 |
| T | R | 4.5 | 132.5 | −90.5 |

TABLE 6

| Tester | Flex | Shaft torque providing best ease of swinging | Index value (B) $\omega z\_top$ | Index value (C) $\omega z\_top\sim\omega y\_max/t\_top\sim\omega y\_max$ |
|---|---|---|---|---|
| A | X | 3.5 | 8.8 | −447.4 |
| B | X | 3.0 | −45.8 | 10.1 |
| E | X | 3.0 | −64.2 | −71.0 |
| F | S | 3.5 | −1.2 | −354.9 |
| H | S | 4.5 | 51.1 | −364.0 |
| J | S | 3.5 | 49.2 | 120.0 |
| K | S | 3.5 | 66.2 | −338.7 |
| L | S | 4.5 | 117.0 | −298.3 |
| M | S | 5.0 | 118.0 | −245.0 |
| N | S | 3.5 | 14.2 | −275.2 |
| O | S | 5.0 | 99.6 | −22.1 |
| P | R | 4.5 | 94.0 | 186.1 |
| Q | R | 4.5 | 94.0 | 243.6 |
| R | R | 4.5 | 84.6 | −432.2 |
| S | R | 4.0 | 33.5 | −488.4 |
| T | R | 4.5 | 132.5 | −90.5 |
| C | X | 3.0 | 39.1 | −609.1 |
| D | X | 3.5 | 85.1 | −909.8 |
| G | S | 4.0 | 61.3 | −591.3 |
| I | S | 3.5 | 100.0 | −571.0 |

Figure 14:
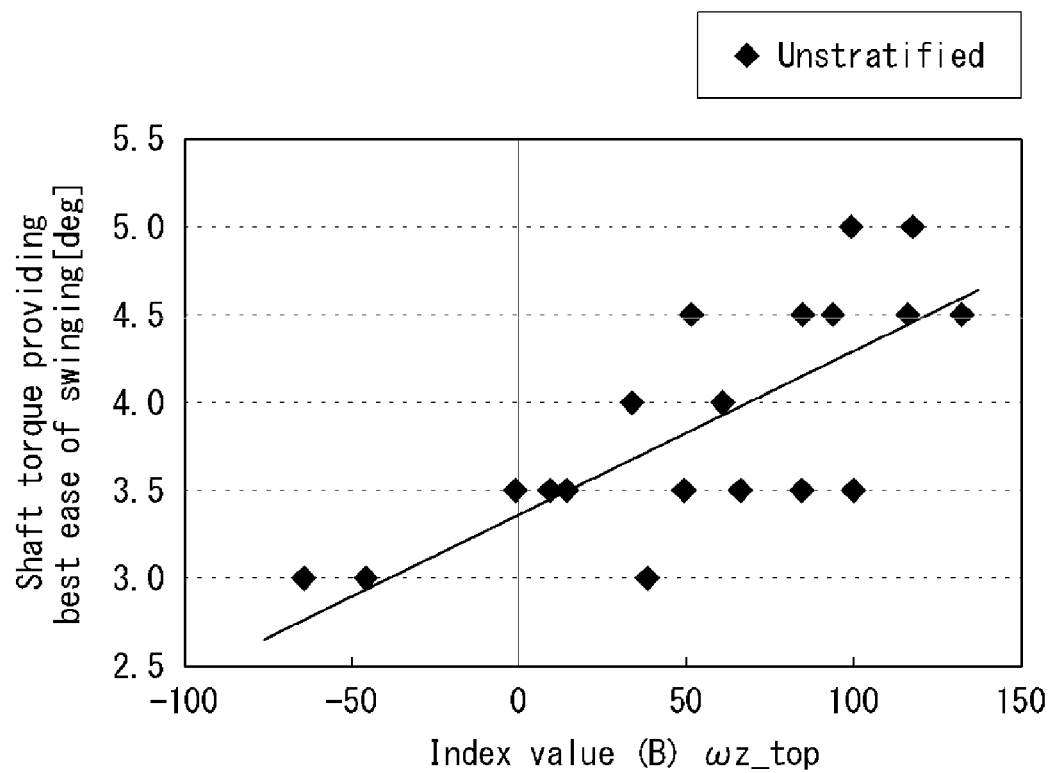
FIG. 14 shows an example of a relationship between an index value of the present invention and a shaft torque providing ease of swinging, and contains unstratified data.
Figure 15:
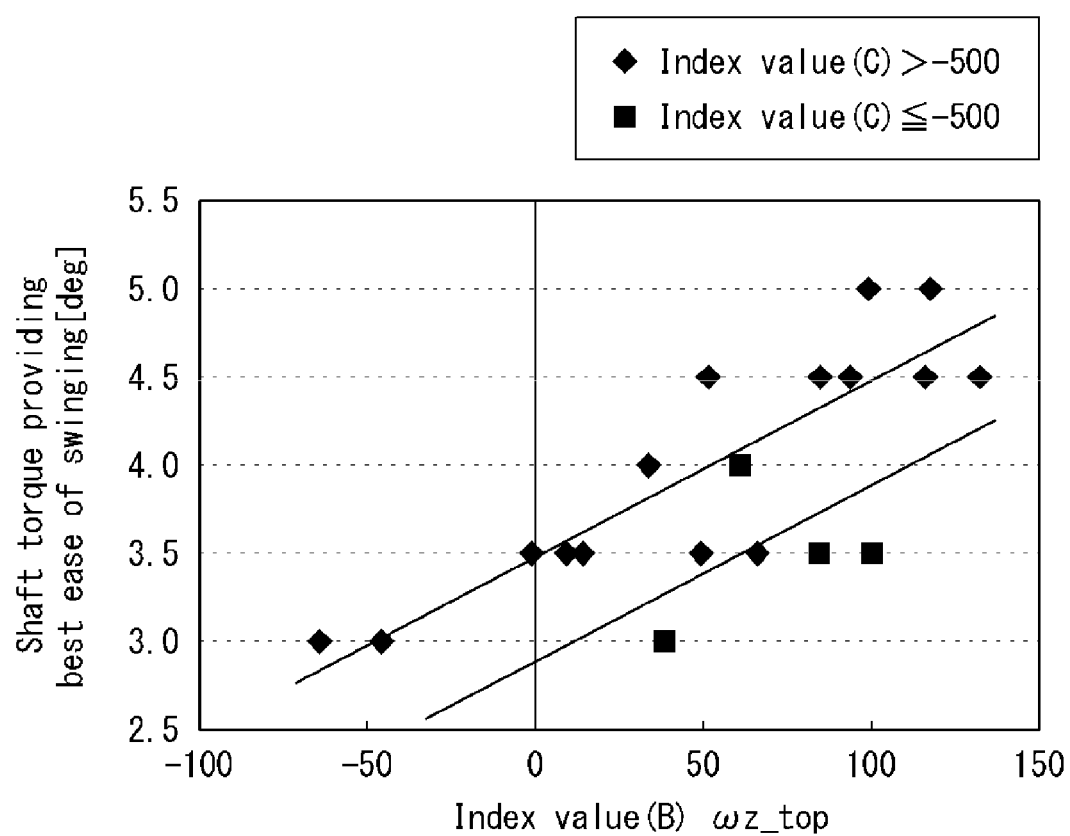
FIG. 15 shows an example of a relationship between the index value of the present invention and a shaft torque providing ease of swinging, and contains stratified data.

Stratification by another index value was not performed in Table 3 (FIG. 12) and Table 5 (FIG. 14), whereas stratification by another index value was performed in Table 4 (FIG. 13) and Table 6 (FIG. 15). In Table 4 (FIG. 13), stratification was performed between cases where the index value (B) was not lower than 20 and cases where the index value (B) was lower than 20. In Table 6 (FIG. 15), stratification was performed between cases where the index value (C) was not higher than −500 and cases where the index value (C) was higher than −500.

[Second Embodiment]

In the present embodiment, unlike in the first embodiment, fitting is performed based on respective twist rigidities at multiple parts along the shaft axial direction.

Figure 16:
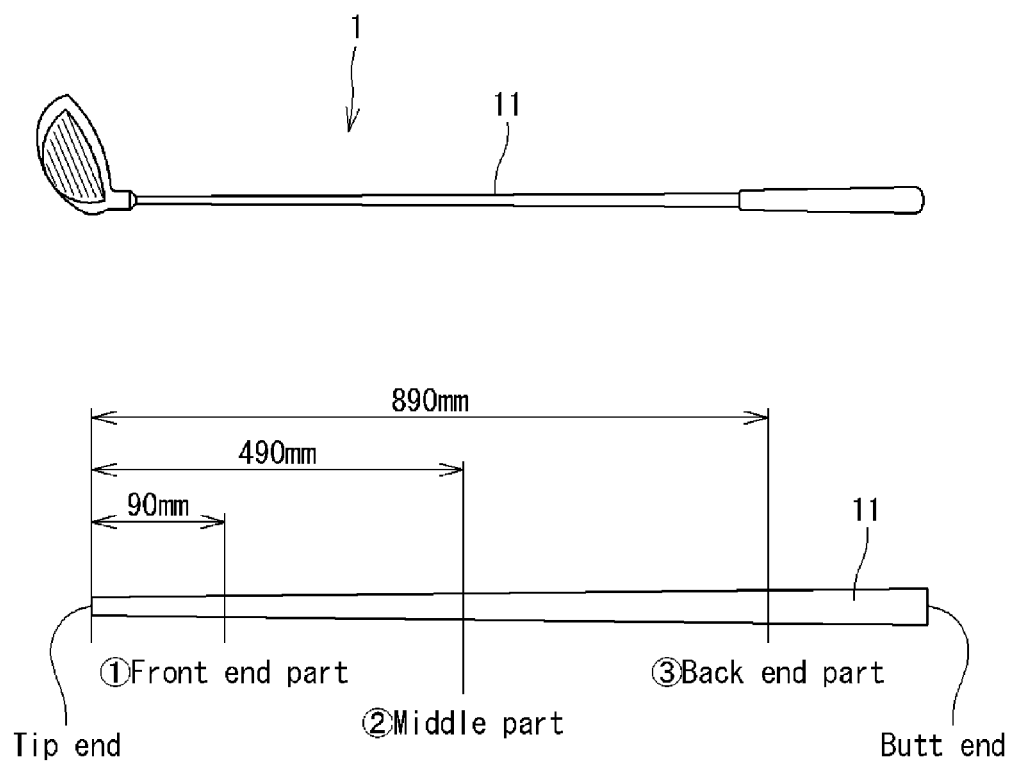
FIG. 16 is for describing three parts along an axial direction of a shaft.
Figure 17:
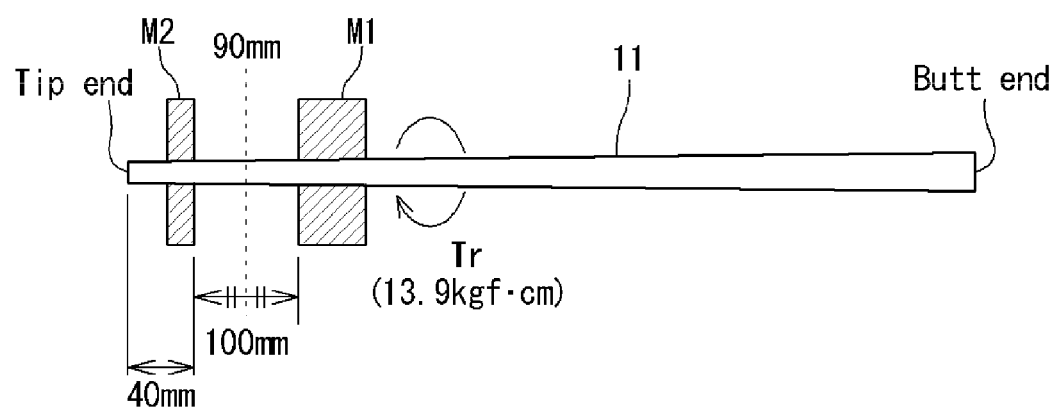
FIG. 17 is for describing a method for measuring a twist rigidity at a front end part of the shaft.
Figure 18:
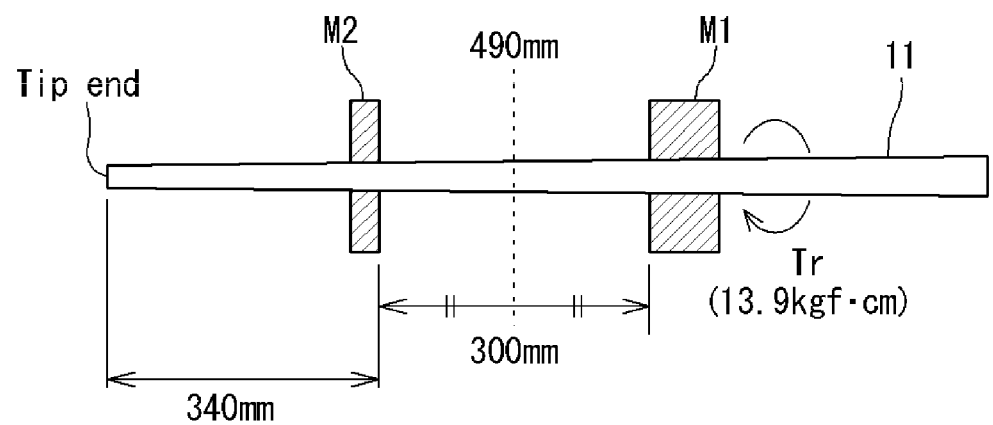
FIG. 18 is for describing a method for measuring a twist rigidity at a middle part of the shaft.
Figure 19:
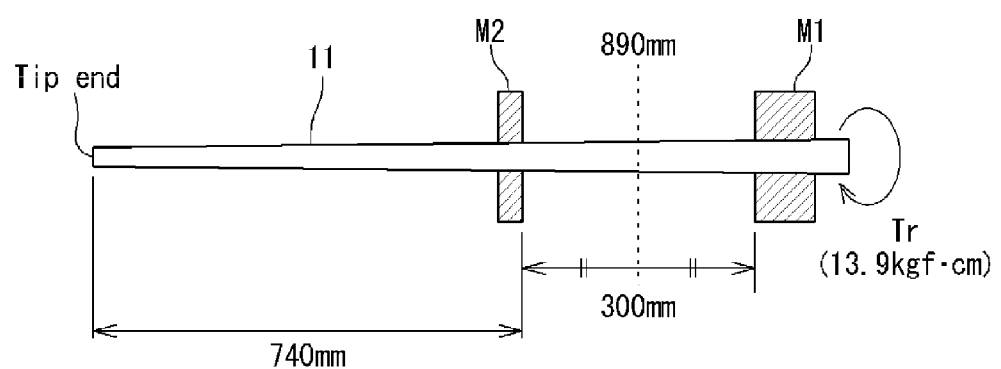
FIG. 19 is for describing a method for measuring a twist rigidity at a back end part of the shaft.

FIG. 16 is for describing parts of the shaft 11 of the golf club 1 where the twist rigidity is measured in the present embodiment. In the present embodiment, the twist rigidity is measured at multiple parts along the axial direction of the shaft 11. Specifically, the twist rigidity is measured at three parts, i.e., the front end part, the middle part, and the back end part, of the shaft 11. A twist rigidity at a part located 90 mm away from the tip end of the shaft 11 is measured as the front end part, a twist rigidity at a part located 490 mm away from the tip end of the shaft 11 is measured as the middle part, and a twist rigidity at a part located 890 mm away from the tip end of the shaft 11 is measured as the back end part.

In the present embodiment, although the twist rigidity is measured at three parts of the shaft 11, the twist rigidity may be measured, for example, at two parts, a front part and a back part, or the twist rigidity may be measured at four different parts along the axial direction of the shaft 11.

In addition, in the present embodiment, although a part located 90 mm away from the tip end of the shaft 11 is used as the front end part of the shaft 11, a part located within a range of 50 to 150 mm away from the tip end can be used as the front end part. Similarly, in the present embodiment, although a part located 490 mm away from the tip end of the shaft 11 is used as the middle part of the shaft 11, a part located within a range of 400 to 600 mm away from the tip end can be used as the middle part. Furthermore, in the present embodiment, although a part located 890 mm away from the tip end of the shaft 11 is used as the back end part of the shaft 11, a part located within a range of 800 to 1000 mm away from the tip end can be used as the back end part.

Figure 12:
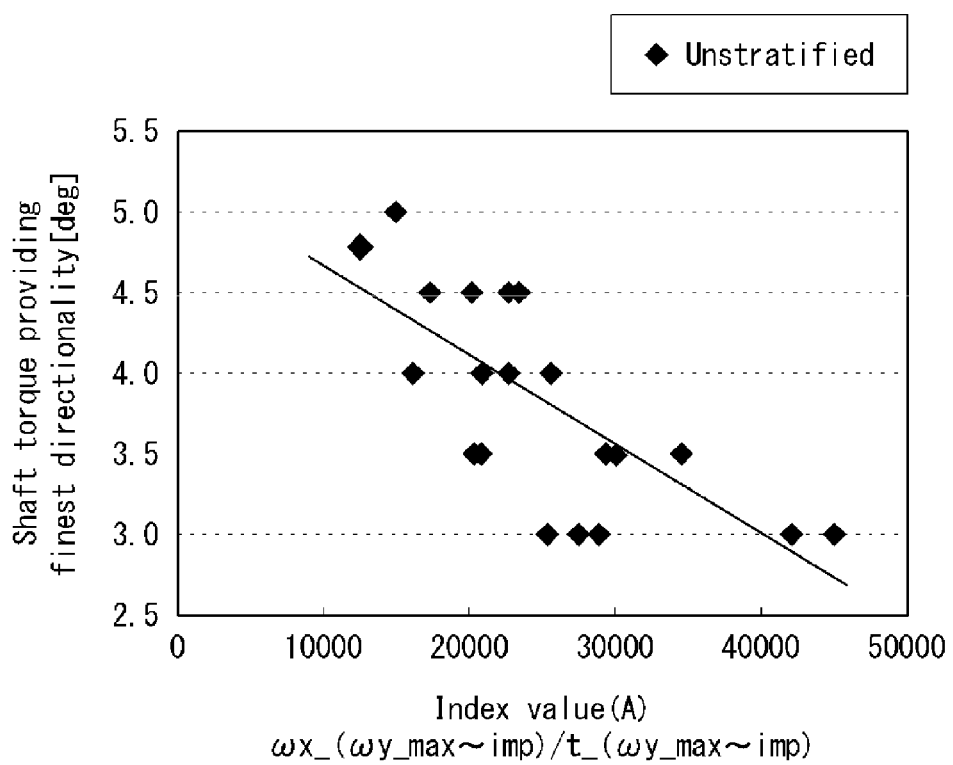
FIG. 12 shows an example of a relationship between an index value of the present invention and a shaft torque providing fine directionality, and contains unstratified data.
Figure 13:
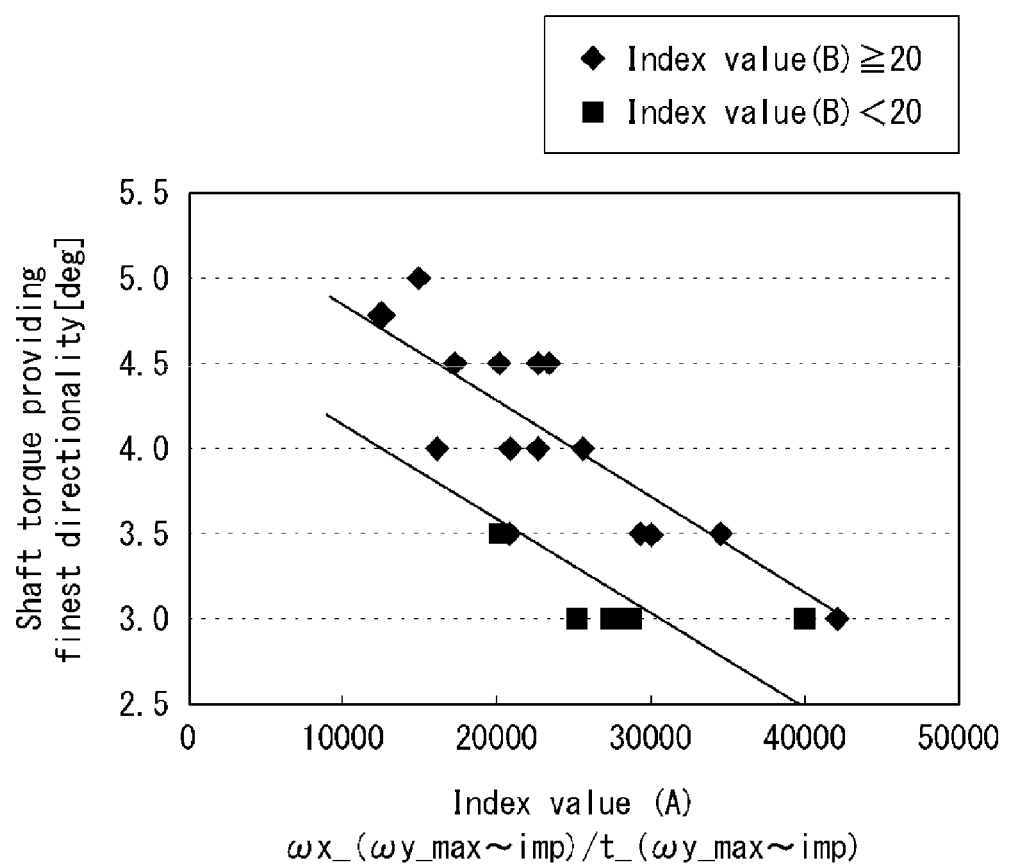
FIG. 13 shows an example of a relationship between the index value of the present invention and a shaft torque providing fine directionality, and contains stratified data.

FIGS. 12 to 14 are for describing the method for measuring the twist rigidity (GJ) respectively at the front end part (90 mm away from the tip end), the middle part (490 mm away from the tip end), and the back end part (890 mm away from the tip end) of the shaft 11 of the golf club 1. Regarding the twist rigidity GJ, "G" represents elastic shear modulus (modulus of transverse elasticity), and, similarly, "J" represents torsional constant (cross-section torsional moment).

In this measuring method, with respect to a part where the twist rigidity is to be measured, the front end of the shaft 11 is unrotatably fixed by the jig M2 and the back end of the shaft 11 is held by the jig M1. As shown in FIGS. 12 to 14, the positions of the jig M1 and the jig M2 differ depending on the part where the twist rigidity is to be measured. For example, when the twist rigidity of the front end part (90 mm away from the tip end) is to be measured, the jig M1 is arranged such that an end part on its tip end side is located 140 mm away from the tip end, whereas the jig M2 is arranged such that an end part on its butt end side is located 40 mm away from the tip end. The distance between the end part on the butt end side of the jig M2 and the end part on the tip end side of the jig M1 is set to 100 mm such that the part located 90 mm away from the tip end is positioned just in the middle between the end part on the butt end side of the jig M2 and the end part on the tip end side of the jig M1. The same applies for the middle part (490 mm away from the tip end) and the back end part (890 mm away from the tip end), and the positions of the jig M1 and the jig M2 are set such that the middle part or the back end part is positioned just in the middle between the jig M1 and the jig M2.

When the twist rigidity of the front end part (90 mm away from the tip end) is to be measured, a torque Tr of 13.9 kgf·cm is applied to a position located 40 mm away from the tip end. When the twist rigidity of the middle part (490 mm away from the tip end) is to be measured, a torque Tr of 13.9 kg·cm is applied to a position located 340 mm away from the tip end. When the twist rigidity of the back end part (890 mm away from the tip end) is to be measured, a torque Tr of 13.9 kgf·cm is applied to a position located 740 mm away from the tip end.

Then, the twist rigidity value GJ (gf·m$^2$/rad) is calculated from a torsion angle $\theta$ (rad) of the shaft 11 at the above described torque applying position. When the torque, the interval between the jig M1 and the jig M2, and the torsion angle are respectively represented as Tr, 1 (m), and $\theta$; the twist rigidity value GJ can be calculated as GJ=Tr×1/$\theta$ based on Tr=GJ×$\theta$/1.

A rotational velocity of the jig M1 when applying the torque Tr is set equal to or lower than 130 deg/min. Furthermore, when the shaft 11 deforms due to being held by the jig M1 or the jig M2, the measurement is performed after the inside of the shaft 11 is filled with a core material or the like.

[Index Value]

In the present embodiment, among the above described various stages of the swing, focus is placed on the grip angular velocity from around the top to the impact during a downswing, and the angular velocity is subdivided and quantified in accordance with the elapsed time. Then, a shaft of a golf club is selected based on an index value calculated using the quantified value (quantitative value), and a relationship, obtained in advance through test-hitting, between the index value and the twist rigidity that matches a golfer. In more detail, the relationship between the index value and the twist rigidity matching the golfer is obtained in advance through test-hitting at each of the three parts of the shaft (front end part, middle part, and back end part). Then, based on the relationship and the index value calculated from a swing of a golfer hoping for a fitting, a twist rigidity suitable for the golfer is calculated. Such twist rigidity is calculated for each of the three parts of the shaft. Then, from among multiple shafts, a shaft having a twist rigidity characteristic that is closest to the calculated three twist rigidities (the twist rigidity of the front end part, the twist rigidity of the middle part, and the twist rigidity of the back end part) is selected. With regard to the multiple shafts, the twist rigidities of the three parts are measured in advance, and the measured twist rigidity values are stored in a database.

The "index value" in the present embodiment is a value calculated by quantifying the grip angular velocity, and is a value that is recognized to correlate with the twist rigidity matching a golfer. Examples of such "index value" include those shown in the following. It should be noted that a match with a golfer includes a case where evaluation is performed objectively based on such as standard deviation σ of scattering to the left and right of a hit ball for the directionality of a hit ball, and a case where evaluation is performed through a sensory test (interview survey) of a golfer for the ease of swinging a club.

It should be noted that, with a left-handed golfer, the angular velocity about the x-axis and the angular velocity about the z-axis are each inverted with respect to a right-handed golfer. That is, plus and minus each become opposite. Thus, the following description relates to a right-handed golfer, and description regarding a left-handed golfer will be provided after being specifically noted.

<Improvement in Directionality>

(1) Index Value (A): Magnitude of Change Amount of Grip Angular Velocity about x-Axis Per Unit of Time, from when Grip Angular Velocity about y-Axis Becomes Maximum to when Impact Occurs This index value (A) is a value that is recognized to correlate with the torque matching a golfer particularly in terms of improving directionality of a hit ball. Directionality of a hit ball is determined by the direction of a club face immediately before impact, and a club face angle is highly correlated with the change amount of the grip angular velocity about the x-axis immediately before the impact. Thus, when the change amount of the angular velocity about the x-axis immediately before the impact is higher, the club head is accelerated more rapidly and the club face direction easily becomes open or is easily upset at the moment of the impact. When a shaft having a low torque (a shaft having high twist rigidity) is selected for such a golfer, since variation of the club face angle becomes small and opening of the club face is suppressed, directionality of a hit ball improves. Similarly in an opposite case, when the change amount of the angular velocity about the x-axis immediately before the impact is low, the club face cannot be actively set open and the ball is easily yanked, resulting in deterioration of directionality of a hit ball. In addition, when the club face cannot be set open, the flight distance becomes small since the loft angle upon impact becomes insufficient. When a shaft having a high torque (a shaft having low twist rigidity) is selected for such a golfer, the club face is set open properly, directionality of a hit ball improves, and a larger flight distance is obtained since a proper loft angle is obtained.

The index value (A) is calculated as described next.

First, from the waveform of the grip angular velocity coy about the y-axis, $t_{\omega y\_max\sim imp}$, which is a time (t1) from when the grip angular velocity about the y-axis becomes maximum during a downswing from when the impact occurs, is calculated.

Next, $\omega x_{\omega y\_max\sim imp}$, which is an average value (m1) of the grip angular velocity about the x-axis from when the grip angular velocity about the y-axis becomes maximum during a downswing to when the impact occurs, is calculated.

Then, by dividing the average value (m1) by the time (t1), the index value (A), which is the magnitude of the change amount of the grip angular velocity about the x-axis per unit of time from the grip angular velocity about the y-axis becomes maximum to when the impact occurs, is obtained.

$$\text{Index value }(A) = \omega x_{\omega y\_max\sim imp}/t_{\omega y\_max\sim imp}$$

The twist rigidity GJ (torque) of each of the multiple parts is calculated based on the index value (A) calculated in such manner, and a relationship, obtained in advance through test-hitting, between the index value (A) and the twist rigidity matching a golfer regarding directionality of a hit ball, more specifically, based on an approximate formula representing the relationship of the two.

For example, when $\omega x_{\omega y\_max\sim imp}/t_{\omega y\_max\sim imp}$ is represented as x, the following formulae (7) to (9) representing regression lines obtained through least squares method can be used as the approximate formula.

$$GJ_{90}(gf \cdot m^2/rad) = 0.000678x + 47.3 \tag{7}$$

$$GJ_{490}(gf \cdot m^2/rad) = 0.00414x + 88.8 \tag{8}$$

$$GJ_{890}(gf \cdot m^2/rad) = 0.0105x + 83.3 \tag{8}$$

$GJ_{90}$ is the twist rigidity at the front end part located 90 mm away from the tip end, $GJ_{490}$ is the twist rigidity at the middle part located 490 mm away from the tip end, and $GJ_{890}$ is the twist rigidity at the back end part located 890 mm away from the tip end.

(2) Index Value (B): Change Amount of Grip Angular Velocity about z-Axis Around the Top Although the twist rigidity can be calculated using the approximate formula (e.g., formulae (7) to (9) described above) representing the relationship between the index value (A) and the twist rigidity matching a golfer regarding directionality of a hit ball, it is possible to, for further improving directionality, stratify the relationship between the index value (A) and the twist rigidity by using this index value (B).

The change amount of the grip angular velocity about the z-axis around the top, i.e., $\omega z_{top}$, is positive in a direction in which a club face becomes closed. With a golfer whose $\omega z_{top}$ is positive, in more detail, a golfer whose $\omega z_{top}$ is positive and not lower than a predetermined value, a golf club is swung down while having the right hand covering thereover at the top. Since the covering by the right hand causes the club face to close easily, when a shaft having a low torque (high twist rigidity) is used, the club face does not open during the downswing and the ball is yanked upon impact, or the wrist is used too extensively to cause the club face to open, resulting in deteriorated directionality due to having some balls that cannot be caught or having some sliced balls. Thus, a golfer whose $\omega z_{top}$ is positive preferably selects a shaft having a high torque (low twist rigidity).

On the other hand, with a golfer whose $\omega z_{top}$ is negative or low, since the club face moves in a direction to open, if the impact occurs with the club face being open or a shaft having a high torque is used, the wrist becomes closed to avoid the club face from being too open during the downswing, and yanking or a hook ball occurs easily. Thus, a golfer whose $\omega z_{top}$ is negative or low preferably selects a shaft having a low torque.

As described above, preferably, the relationship between the twist rigidity and the index value (A) is stratified in accordance with the magnitude of $\omega z_{top}$, and one suitable approximate formula among multiple approximate formulae prepared in advance is used.

For example, when $\omega x_{\omega y\_max\sim imp}/t_{\omega y\_max\sim imp}$ is represented as x, the following formulae (10) to (12) representing regression lines obtained through least squares method can be used as the approximate formula (fifth approximate formula) in cases where $\omega z_{top}$ is not lower than 20 (deg/sec), and the following formulae (13) to (15) representing the same can be used as the approximate formula (sixth approximate formula) in cases where $\omega z_{top}$ is lower than 20 (deg/sec).

1) Case: $\omega z_{top} \geq 20$ (deg/see)

$$GJ_{90}(gf \cdot m^2/rad) = 0.000781x + 42.1 \tag{10}$$

$$GJ_{490}(g \cdot m^2/rad) = 0.00417x + 81.0 \tag{11}$$

$$GJ_{890}(gf \cdot m^2/rad) = 0.0104x + 70.9 \tag{12}$$

2) Case: $\omega z_{top} < 20$ (deg/sec)

$$GJ_{90}(gf \cdot m^2/rad) = 0.000781x + 50.5 \tag{13}$$

$$GJ_{490}(gf \cdot m^2/rad) = 0.00417x + 111.0 \tag{14}$$

$$GJ_{890}(gf \cdot m^2/rad) = 0.0104x + 140.0 \tag{15}$$

[Case with Left-Handed Golfer]

In a left-handed golfer, the angular velocity about the x-axis and the angular velocity about the z-axis are each inverted with respect to a right-handed golfer. With regard to the index value (A), $\omega x_{\omega y\_max\text{-}imp}$ becomes inverted. Thus, when the change amount of the angular velocity about the x-axis immediately before impact is negatively larger, the club head is accelerated more rapidly and the club face direction easily becomes open or is easily upset at the moment of the impact. The formulae (7) to (9) for calculating the twist rigidity of each of the parts for a right-handed golfer respectively become the following formulae (7)' to (9)' with a left-handed golfer.

$$GJ_{90}(\text{gf}\cdot\text{m}^2/\text{rad})=-0.000678x+47.3 \quad (7)'$$

$$GJ_{490}(\text{gf}\cdot\text{m}^2/\text{rad})=-0.00414x+88.8 \quad (8)'$$

$$GJ_{890}(\text{gf}\cdot\text{m}^2/\text{rad})=-0.0105x+83.3 \quad (9)'$$

In addition, the condition ($\omega z_{\_top}$) for performing the stratification with a left-handed golfer becomes inverted. Thus, with a left-handed golfer whose $\omega z_{\_top}$ is negative, a golf club is swung down while having the left hand covering thereover at the top. The formulae (10) to (15) for a right-handed golfer respectively become the following formulae (10)' to (15)' with a left-handed golfer.

1) Case: $\omega z_{\_top} < -20$ (deg/sec)

$$GJ_{90}(\text{gf}\cdot\text{m}^2/\text{rad})=-0.000781x+42.1 \quad (10)'$$

$$GJ_{490}(\text{gf}\cdot\text{m}^2/\text{rad})=-0.00417x+81.0 \quad (11)'$$

$$GJ_{890}(\text{gf}\cdot\text{m}^2/\text{rad})=-0.0104x+70.9 \quad (12)'$$

2) Case: $\omega z_{\_top} > -20$ (deg/sec)

$$GJ_{90}(\text{gf}\cdot\text{m}^2/\text{rad})=-0.000781x+50.5 \quad (13)'$$

$$GJ_{490}(\text{gf}\cdot\text{m}^2/\text{rad})=-0.00417x+111.0 \quad (14)'$$

$$GJ_{890}(\text{gf}\cdot\text{m}^2/\text{rad})=-0.0104x+140.0 \quad (15)'$$

<Improvement in Ease of Swinging>

Although the index value (B) can be used for stratification when calculating the twist rigidity using the index value (A), the index value (B) itself is a value that is recognized to correlate with the twist rigidity matching a golfer particularly in terms of improving the ease of swinging. Thus, the twist rigidity can also be calculated by using the index value (B).

The ease of swinging a golf club refers to the ease of matching the timing, and it is thought that a swing is sensed as being easy when the swing and torsion of the shaft synchronize. In the present invention, when various tests (test-hitting) were performed and the ease of swinging was scored using questionnaires to examine its correlation with swing index values, it was revealed that the ease of swinging a golf club highly correlates with $\omega z_{\_top}$, which is the change amount of the grip angular velocity about the z-axis around the top. Thus, it is thought that a phenomenon similar to that observed in the stratification of fitting focusing on directionality described above is occurring, and the index value (B) is linked to the timing of the impact.

Thus, the twist rigidity of each of the multiple parts can be calculated based on the index value (B) and a relationship, obtained in advance through test-hitting, between the index value (B) and the twist rigidity of each of the multiple parts matching a golfer regarding the ease of swinging a golf club, more specifically, based on the approximate formula representing the relationship of the two.

For example, when $\omega z_{\_top}$ is represented as x, the following formulae (16) to (18) representing regression lines obtained through least squares method can be used as the approximate formula.

$$GJ_{90}(\text{gf}\cdot\text{m}^2/\text{rad})=-0.0897x+69.4 \quad (16)$$

$$GJ_{490}(\text{gf}\cdot\text{m}^2/\text{rad})=-0.527x+223.7 \quad (17)$$

$$GJ_{890}(\text{gf}\cdot\text{m}^2/\text{rad})=-1.29x+418.3 \quad (18)$$

(3) Index Value (C): Magnitude of Change Amount of the Grip Angular Velocity about z-Axis from when the Top is Reached to when Grip Angular Velocity about y-Axis Becomes Maximum During Downswing Although the twist rigidity can be calculated using the approximate formula (e.g., formulae (16) to (18) described above) representing the relationship between the index value (B) and the twist rigidity matching a golfer regarding the ease of swinging a golf club, it is possible to, for further improving the ease of swinging, stratify the relationship between the index value (B) and the twist rigidity by using this index value (C).

The index value (C) can be calculated in the following manner.

First, from the waveform of the grip angular velocity $\omega y$ about the y-axis, $t_{\_top\text{-}\omega y\_max}$, which is a time (t2) from when the top is reached to when the grip angular velocity about the y-axis becomes maximum during a downswing, is calculated.

Next, $\omega z_{\_top\text{-}\omega y\_max}$, which is an average value (m2) of the grip angular velocity about the z-axis from when the top is reached to when the grip angular velocity about the y-axis becomes maximum during a downswing, is calculated.

Then, by dividing the average value (m2) by the time (t2), the index value (C), which is the magnitude of the change amount of the grip angular velocity about the z-axis from when the top is reached to when the grip angular velocity about the y-axis becomes maximum during the downswing, is obtained.

$$\text{Index value }(C)=\omega z_{\_top\text{-}\omega y\_max}/t_{\_top\text{-}\omega y\_max}$$

With a golfer whose index value (C) is high, the change amount of shaft torsion (in a club face opening direction) at the beginning of a downswing is high. Particularly when the index value (C) is negative and an absolute value thereof is high, the club face is actively set open. Thus, when a shaft having a high torque (low twist rigidity) is used, it becomes difficult to match the timing and the feeling deteriorates since the club face is set too open or varies too much. Therefore, a golfer whose index value (C) is high preferably selects a shaft having a low torque (high twist rigidity).

On the other hand, since a golfer whose index value (C) is low, i.e., whose change amount of the angular velocity is low, does not actively open or close the club face; when a shaft having a low torque is used, rotation of the club face does not occur and the shaft may present a hard sensation. Therefore, a golfer whose index value (C) is low preferably selects a shaft having a high torque (low twist rigidity).

As described above, preferably, the relationship between the twist rigidity and the index value (B) is stratified in accordance with the magnitude of $\omega z_{\_top\text{-}y\_max}/t_{\_top\text{-}\omega y\_max}$, and one suitable approximate formula among multiple approximate formulae prepared in advance is used.

For example, when $\omega z_{\_top}$ is represented as x, the following formulae (19) to (21) representing regression lines obtained through least squares method can be used as the approximate formula (seventh approximate formula) in cases where $\omega z_{\_top-\omega y\_max}/t_{\_top-\omega y\_max}$ is higher than $-500$ (deg/s$^2$), and the following formulae (22) to (24) representing the same can be used as the approximate formula (eighth approximate formula) in cases where $\omega z_{\_top-\omega y\_max}/t_{\_top-\omega y\_max}$ is not higher than $-500$ (deg/s$^2$).

1) Case: $\omega z_{\_top-\omega y\_max}/t_{\_top-\omega y\_max} > -500$ (deg/s$^2$)

$$GJ_{90}(gf \cdot m^2/rad) = -0.0894x + 68.5 \quad (19)$$

$$GJ_{490}(gf \cdot m^2/rad) = -0.531x + 220.1 \quad (20)$$

$$GJ_{890}(gf \cdot m^2/rad) = -1.39x + 406.2 \quad (21)$$

2) Case: $\omega z_{\_top-\omega y\_max}/t_{\_top-\omega y\_max} \leq -500$ (deg/s$^2$)

$$GJ_{90}(gf \cdot m^2/rad) = -0.0894x + 75.5 \quad (22)$$

$$GJ_{490}(gf \cdot m^2/rad) = -0.531x + 237.5 \quad (23)$$

$$GJ_{890}(gf \cdot m^2/rad) = -1.39x + 490.0 \quad (24)$$

[Case with Left-Handed Golfer]

In a left-handed golfer, the angular velocity about the x-axis and the angular velocity about the z-axis are each inverted with respect to a right-handed golfer. More specifically, since the signs of the index value (A) and the index value (B) become inverted, the slopes of the regression lines indicated by the formulae (16) to (18) each become inverted in terms of positive and negative. Furthermore, with regard to the formulae (19) to (24), the condition for the stratification and the slopes of the regression lines indicated by the formulae each become inverted.

Thus, the formulae (16) to (18) for a right-handed golfer respectively become the following formulae (16)' to (18)' with a left-handed golfer.

$$GJ_{90}(gf \cdot m^2/rad) = 0.0897x + 69.4 \quad (16)'$$

$$GJ_{490}(gf \cdot m^2/rad) = 0.527x + 223.7 \quad (17)'$$

$$GJ_{890}(gf \cdot m^2/rad) = 1.29x + 418.3 \quad (18)'$$

Furthermore, the formulae (13) to (18) for a right-handed golfer respectively become the following formulae (13)' to (18)' with a left-handed golfer.

1) Case: $\omega z_{\_top-\omega y\_max}/t_{\_top-\omega y\_max} < 500$ (deg/s$^2$)

$$GJ_{90}(gf \cdot m^2/rad) = 0.0894x + 68.5 \quad (19)'$$

$$GJ_{490}(gf \cdot m^2/rad) = 0.531x + 220.1 \quad (20)'$$

$$GJ_{890}(gf \cdot m^2/rad) = 1.39x + 406.2 \quad (21)'$$

2) Case: $\omega z_{\_top-\omega y\_max}/t_{\_top-\omega y\_max} \geq -500$ (deg/s$^2$)

$$GJ_{90}(gf \cdot m^2/rad) = 0.0894x + 75.5 \quad (22)'$$

$$GJ_{490}(gf \cdot m^2/rad) = 0.531x + 237.5 \quad (23)'$$

$$GJ_{890}(gf \cdot m^2/rad) = 1.39x + 490.0 \quad (24)'$$

[How to Obtain Approximate Formula]

For example, the approximate formula can be obtained as described in the following.

As testers, twenty right-handed males having a handicap of 2 to 20 were gathered. As a golf club, SRIXON Z-TX2 (club length: 45.0 inches, loft angle: 9.5 degrees) manufactured by Dunlop Sports Co., Ltd., was used. As shown in Table 1, as shafts, 3 types of flexes (corresponding to X/S/R) were prepared, and, for each of the flexes, 5 types of twist rigidities of "high," "intermediate," "low," "front high," and "hand low" were prepared. A head and a shaft were structured to be detachable from each other, and each of the testers performed test-hitting consistently using the same head during the test. A tester with a high trajectory was asked to use a head with a more upright loft, and a tester with a low trajectory was asked to use a head with a more laid loft.

Figure 20:
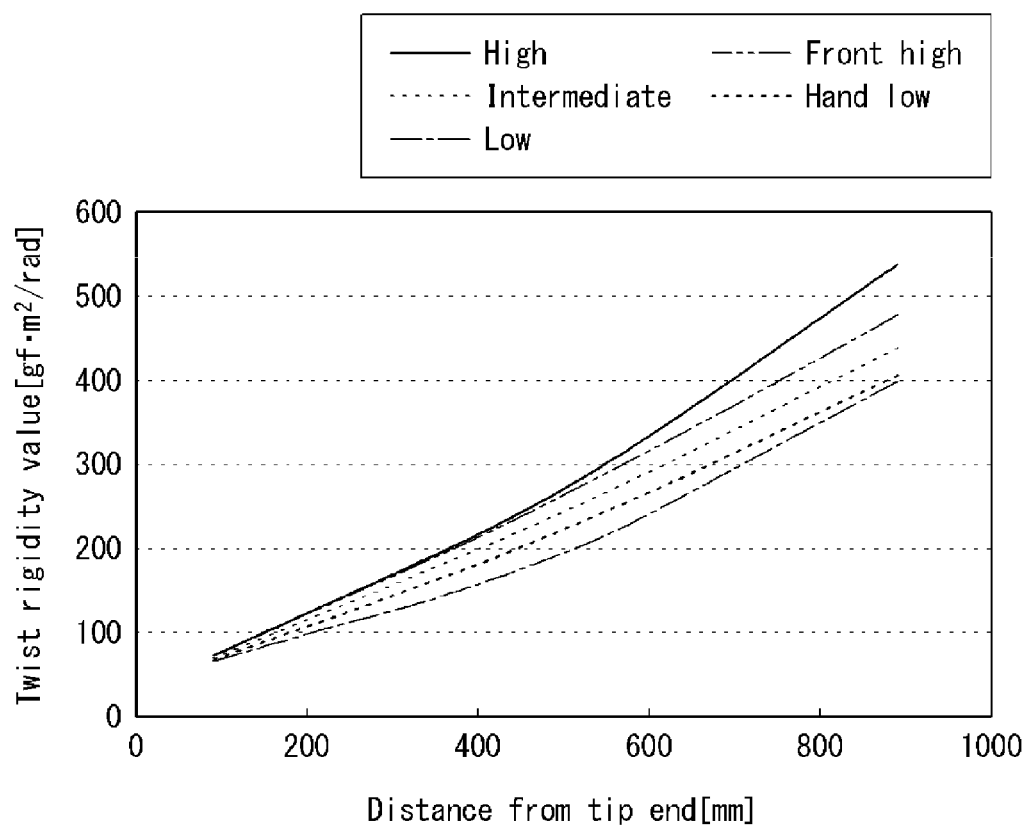
FIG. 20 is for describing 5 types of twist rigidity characteristic.

FIG. 20 shows the twist rigidity characteristic of 5 types of shafts whose flex is "X" among the shafts used in the test. More specifically, FIG. 20 shows a distribution of twist rigidities for shafts whose twist rigidity is of 5 types of "high," "intermediate," "low," "front high," and "hand low." In FIG. 20, the horizontal axis represents the distance (mm) from the tip end of the shaft, and the vertical axis represents a twist rigidity value (gf·m$^2$/rad).

TABLE 7

| Forward Flex | | | Twist rigidity value gf · m$^2$/rad | | |
|---|---|---|---|---|---|
| Flex | mm | Shaft type | 90 mm | 490 mm | 890 mm |
| X | 85 | High | 72.4 | 265.5 | 537.6 |
| | | Intermediate | 70.5 | 238.9 | 438.0 |
| | | Low | 66.2 | 191.4 | 398.2 |
| | | Front high | 72.4 | 258.4 | 477.8 |
| | | Hand low | 67.9 | 218.6 | 405.8 |
| S | 100 | High | 72.4 | 198.9 | 398.2 |
| | | Intermediate | 56.9 | 177.2 | 341.3 |
| | | Low | 56.9 | 149.3 | 252.2 |
| | | Front high | 66.4 | 199.1 | 341.3 |
| | | Hand low | 61.3 | 165.0 | 268.8 |
| R | 110 | High | 66.4 | 199.1 | 341.3 |
| | | Intermediate | 61.3 | 165.0 | 268.8 |
| | | Low | 49.8 | 137.5 | 230.3 |
| | | Front high | 60.2 | 185.6 | 262.4 |
| | | Hand low | 61.3 | 170.7 | 228.1 |

The grip angular velocity was measured using the measuring method that has been described with reference to FIG. 1. SRIXON Z-STAR XV manufactured by Dunlop Sports Co., Ltd., was used as a ball, and the test-hitting was performed using 5 balls for each club (shaft), resulting in a total of 25 balls. However, an obvious miss-shot was excluded, and a redo of the test-hit was performed.

The directionality of a hit ball was evaluated based on standard deviation a of the scattering to the left and right, and a shaft whose a was the smallest was evaluated as a shaft with fine directionality. In addition, the ease of swinging was determined by having each of the testers test-hit 5 balls each for the 5 types of shafts, and then performing an interview survey on each of the testers regarding a shaft that provided the best ease of swinging. The results are shown in Table 8.

TABLE 8

| | Used shaft | Head speed (m/sec) | Shaft type providing finest directionality | | | | | Shaft type providing best ease of swinging | | | | |
|---|---|---|---|---|---|---|---|---|---|---|---|---|
| | | | High | Intermediate | Low | Front high | Hand low | High | Intermediate | Low | Front high | Hand low |
| A | X | 50.2 | ○ | | | | | | | | ○ | |
| B | X | 48.8 | | | | | ○ | | ○ | | | |

TABLE 8-continued

| Used shaft | Head speed (m/sec) | Shaft type providing finest directionality | | | | | Shaft type providing best ease of swinging | | | | |
|---|---|---|---|---|---|---|---|---|---|---|---|
| | | High | Intermediate | Low | Front high | Hand low | High | Intermediate | Low | Front high | Hand low |
| C | X | 47.3 | ○ | | | | | ○ | | | | |
| D | X | 47.1 | | ○ | | | | | ○ | | | |
| E | X | 45.1 | | ○ | | | | | | ○ | | |
| F | S | 45.7 | ○ | | | | | | | | | ○ |
| G | S | 45.0 | | | | ○ | | ○ | | | | |
| H | S | 44.4 | | | | | ○ | | | | | ○ |
| I | S | 44.1 | ○ | | | | | ○ | | | | |
| J | S | 43.2 | ○ | | | | | | | ○ | | |
| K | S | 42.0 | | ○ | | | | ○ | | | | |
| L | S | 41.9 | | | ○ | | | | | ○ | | |
| M | S | 41.8 | | | ○ | | | ○ | | | | |
| N | S | 41.4 | | | | ○ | | | | ○ | | |
| O | S | 40.3 | | | | ○ | | | | ○ | | |
| P | R | 39.2 | | ○ | | | | | | ○ | | |
| Q | R | 39.1 | | | | | ○ | | | | | ○ |
| R | R | 38.9 | ○ | | | | | ○ | | | | |
| S | R | 38.5 | | | ○ | | | ○ | | | | |
| T | R | 37.8 | | | ○ | | | | | | | ○ |

By using data of the measured grip angular velocity, the above described index values (A) to (C) were calculated. The calculation result and a twist rigidity of the shaft providing the finest directionality evaluated using the standard deviation σ of the scattering to the left and right of the hit ball are shown in Tables 9 and 10. In addition, the same calculation result, and the twist rigidity of the shaft providing the best ease of swinging determined by the interview survey are shown in Tables 11 and 12. Stratification by another index value was not performed in Table 9 and Table 11, whereas stratification by another index value was performed in Table 10 and Table 12. In Table 10, stratification was performed between cases where the index value (B) was not lower than 20 and cases where the index value (B) was lower than 20. In Table 12, stratification was performed between cases where the index value (C) was not higher than −500 and cases where the index value (C) was higher than −500.

Figure 21:
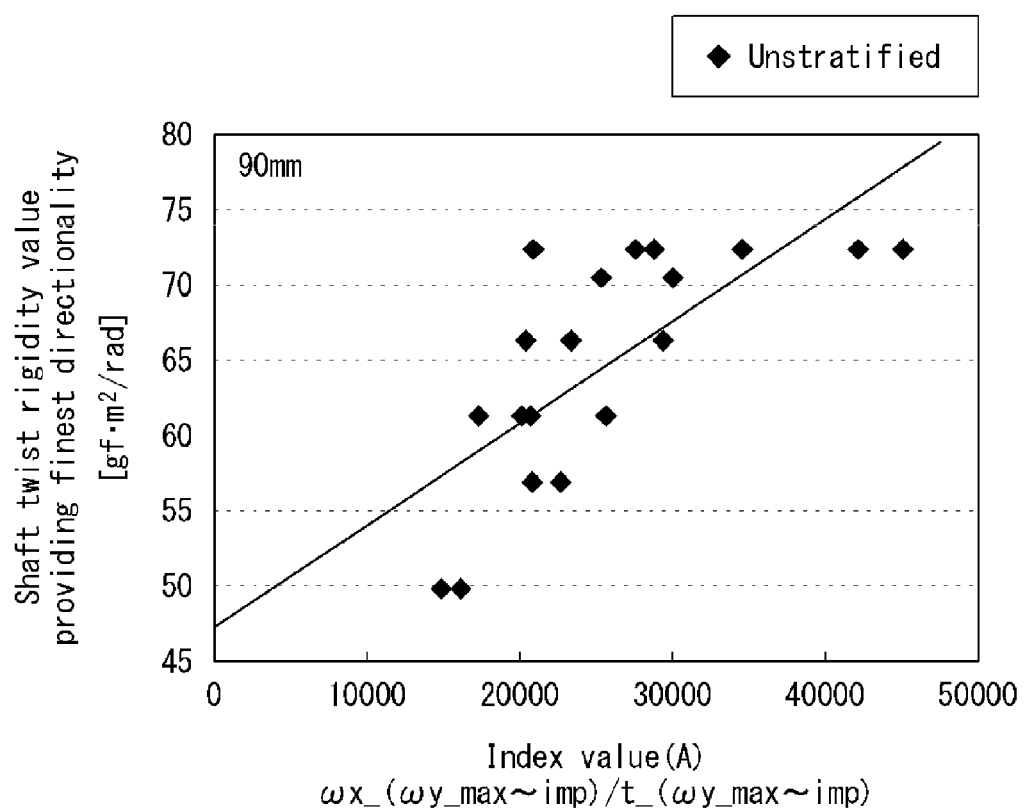
FIG. 21 shows an example of a relationship between the index value of the present invention and a shaft twist rigidity at a shaft front end part (90 mm) providing fine directionality, and contains unstratified data.
Figure 22:
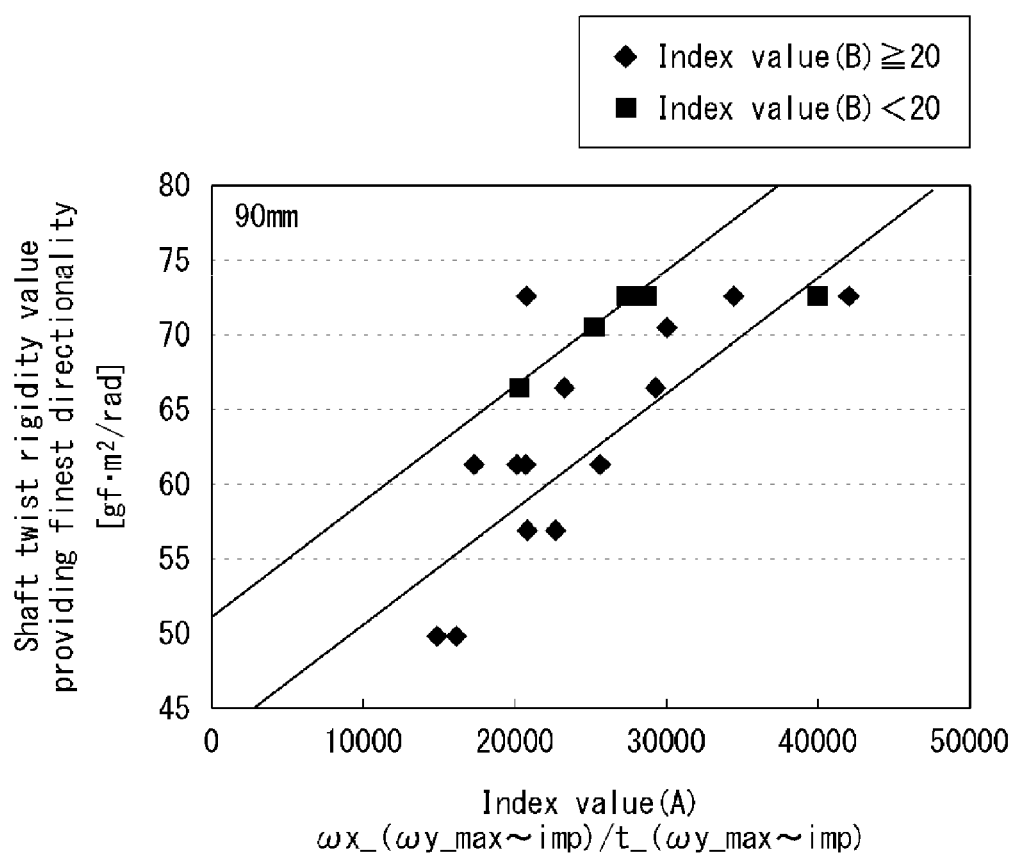
FIG. 22 shows an example of a relationship between the index value of the present invention and a shaft twist rigidity at the shaft front end part (90 mm) providing fine directionality, and contains stratified data.
Figure 23:
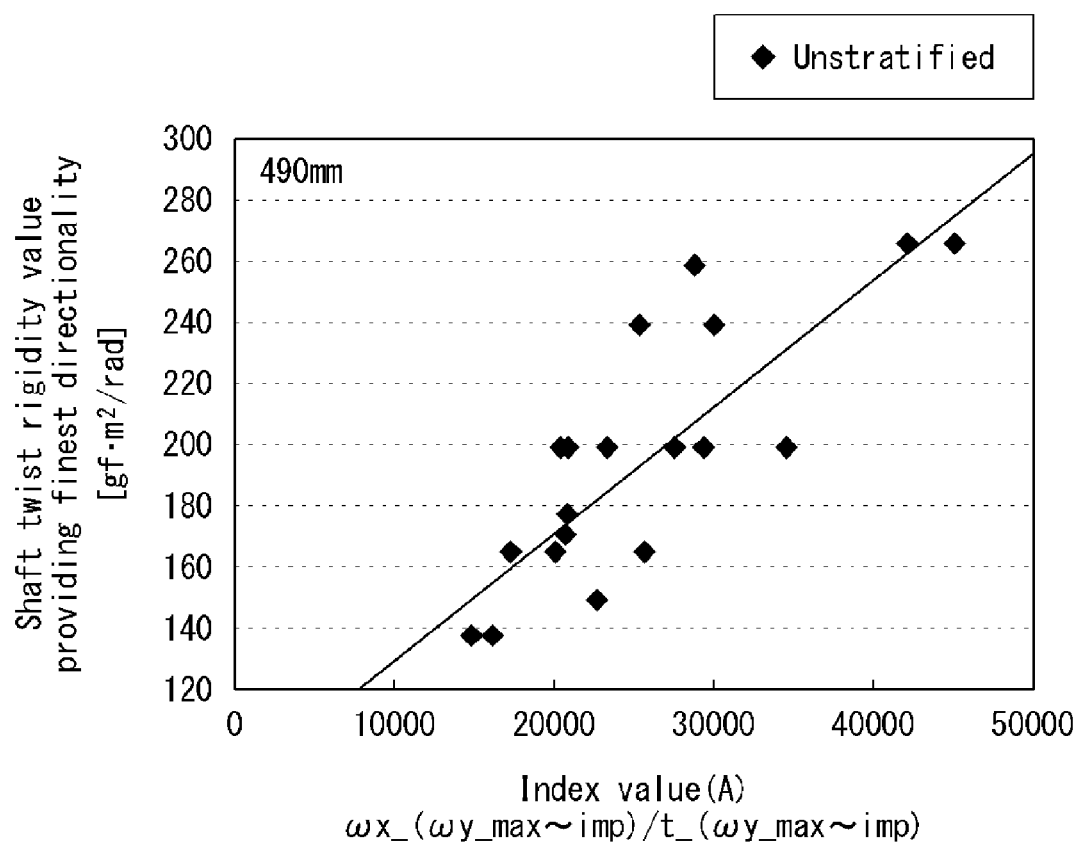
FIG. 23 shows an example of a relationship between the index value of the present invention and a shaft twist rigidity at a shaft middle part (490 mm) providing fine directionality, and contains unstratified data.
Figure 24:
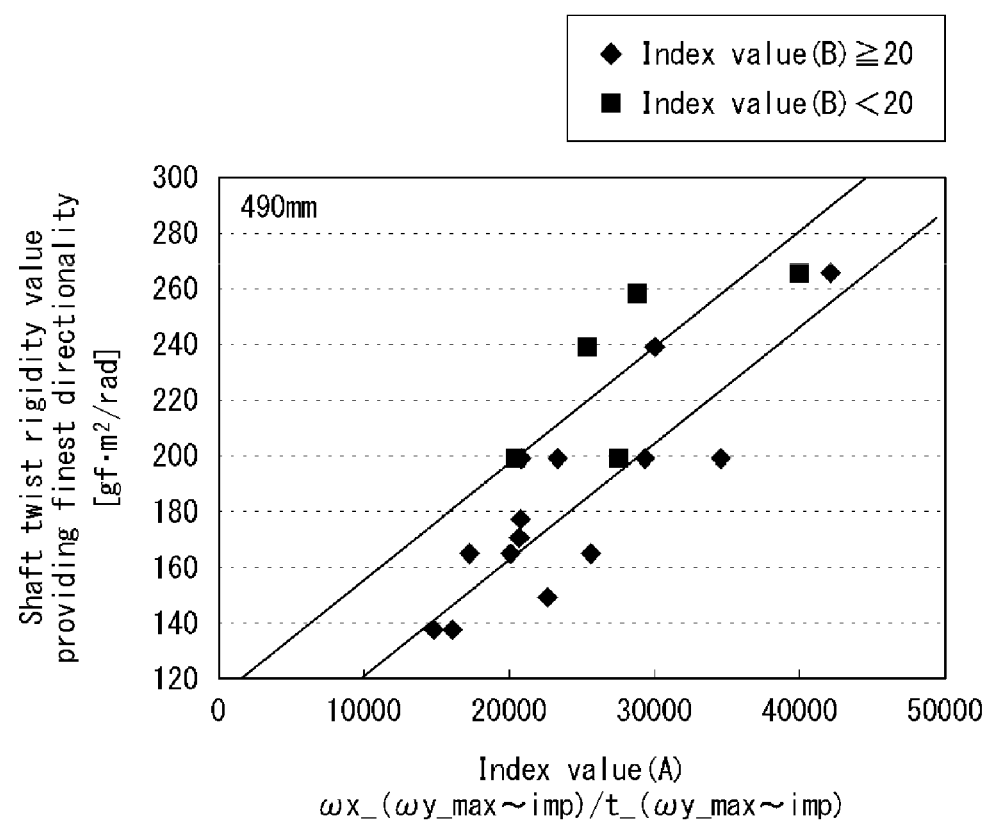
FIG. 24 shows an example of a relationship between the index value of the present invention and a shaft twist rigidity at the shaft middle part (490 mm) providing fine directionality, and contains stratified data.
Figure 25:
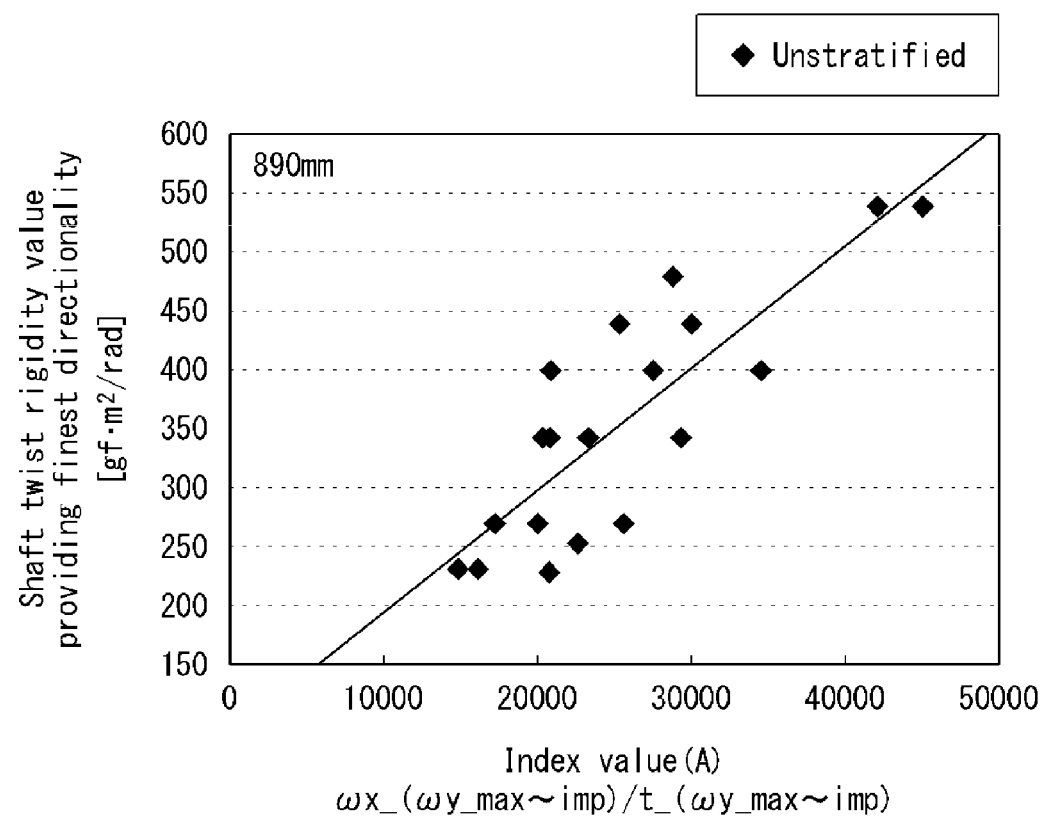
FIG. 25 shows an example of a relationship between the index value of the present invention and a shaft twist rigidity at a shaft back end part (890 mm) providing fine directionality, and contains unstratified data.
Figure 26:
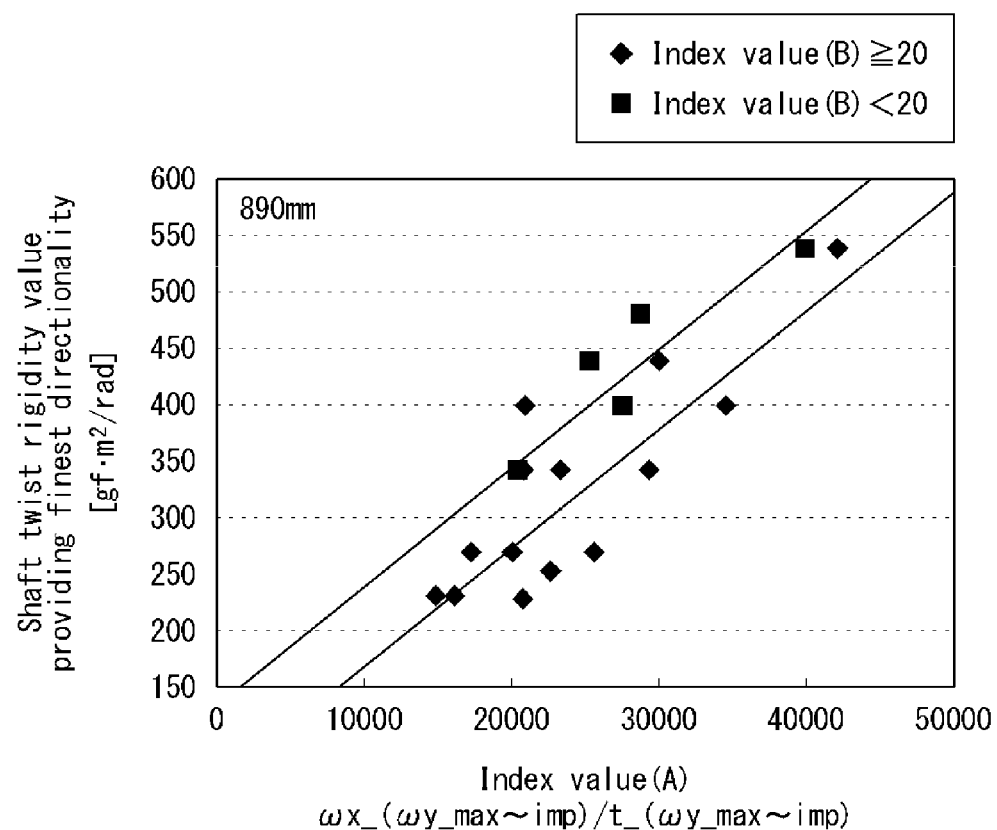
FIG. 26 shows an example of a relationship between the index value of the present invention and a shaft twist rigidity at the shaft back end part (890 mm) providing fine directionality, and contains stratified data.

In addition, FIGS. 21, 23, and 25 corresponding to Table 9 show examples of the relationship between the index value (A) and the shaft twist rigidity at the shaft front end part (90 mm), the shaft middle part (490 mm), and the shaft back end part (890 mm), respectively, providing fine directionality, and contain unstratified data. On the other hand, FIGS. 22, 24, and 26 corresponding to Table 10 show examples of the relationship between the index value (A) and the shaft twist rigidity at the shaft front end part (90 mm), the shaft middle part (490 mm), and the shaft back end part (890 mm), respectively, providing fine directionality, and contain data stratified using the index value (B).

Figure 27:
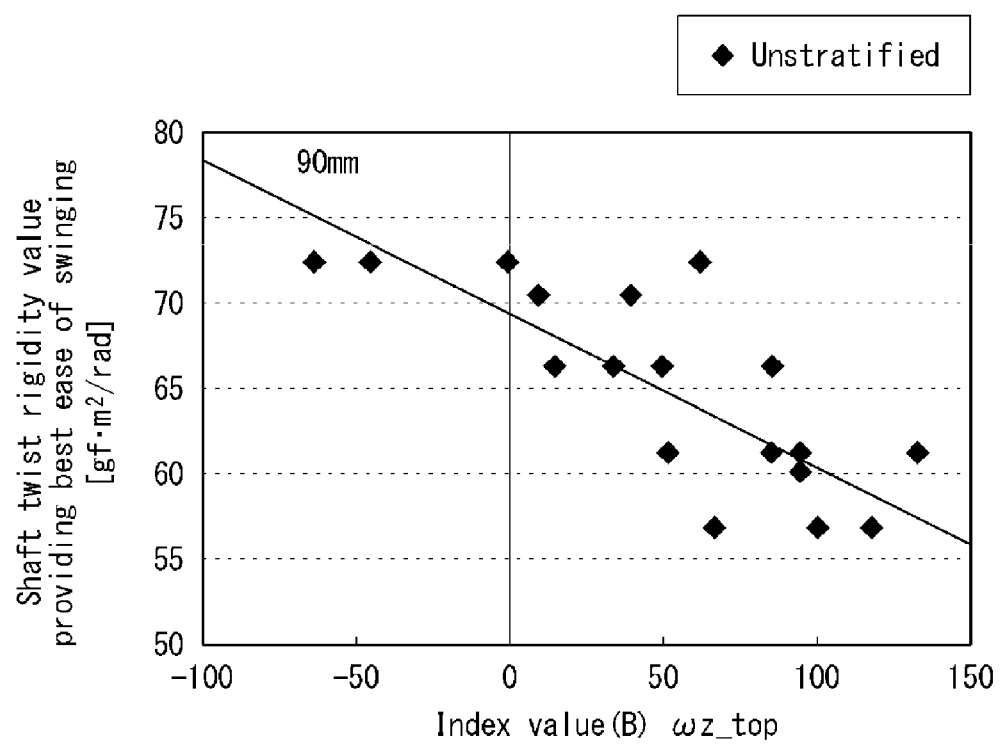
FIG. 27 shows an example of a relationship between the index value of the present invention and a shaft twist rigidity at the shaft front end part (90 mm) providing ease of swinging, and contains unstratified data.
Figure 28:
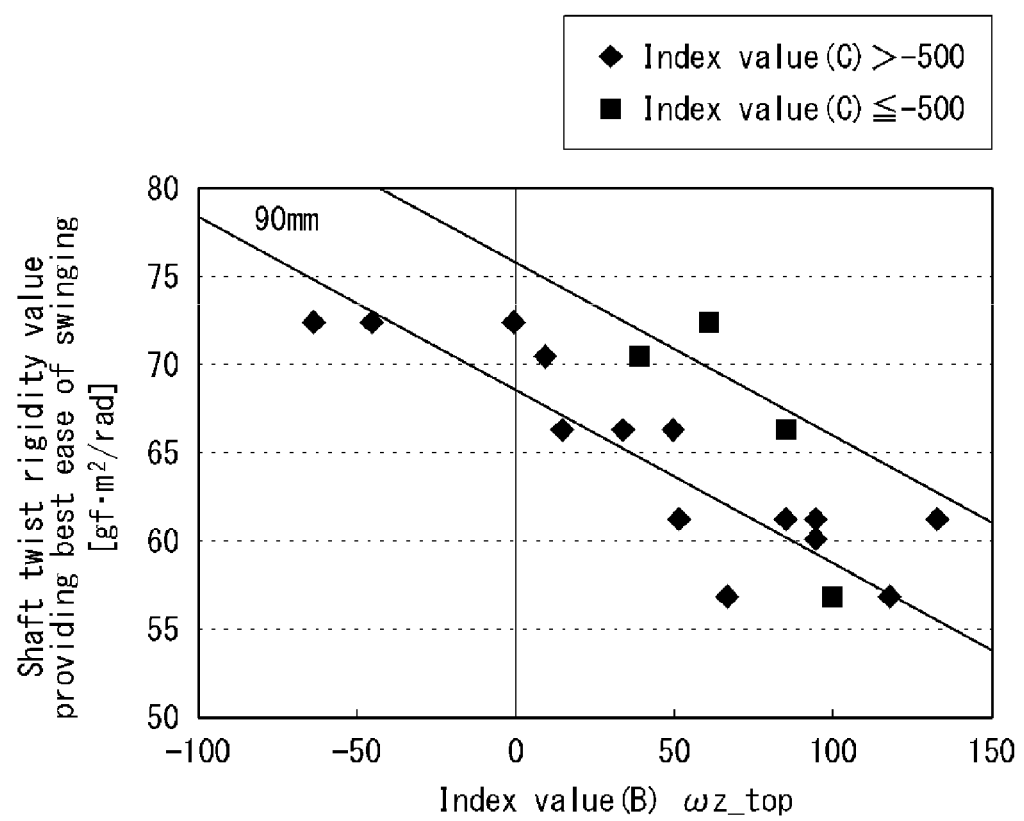
FIG. 28 shows an example of a relationship between the index value of the present invention and a shaft twist rigidity at the shaft front end part (90 mm) providing ease of swinging, and contains stratified data.
Figure 29:
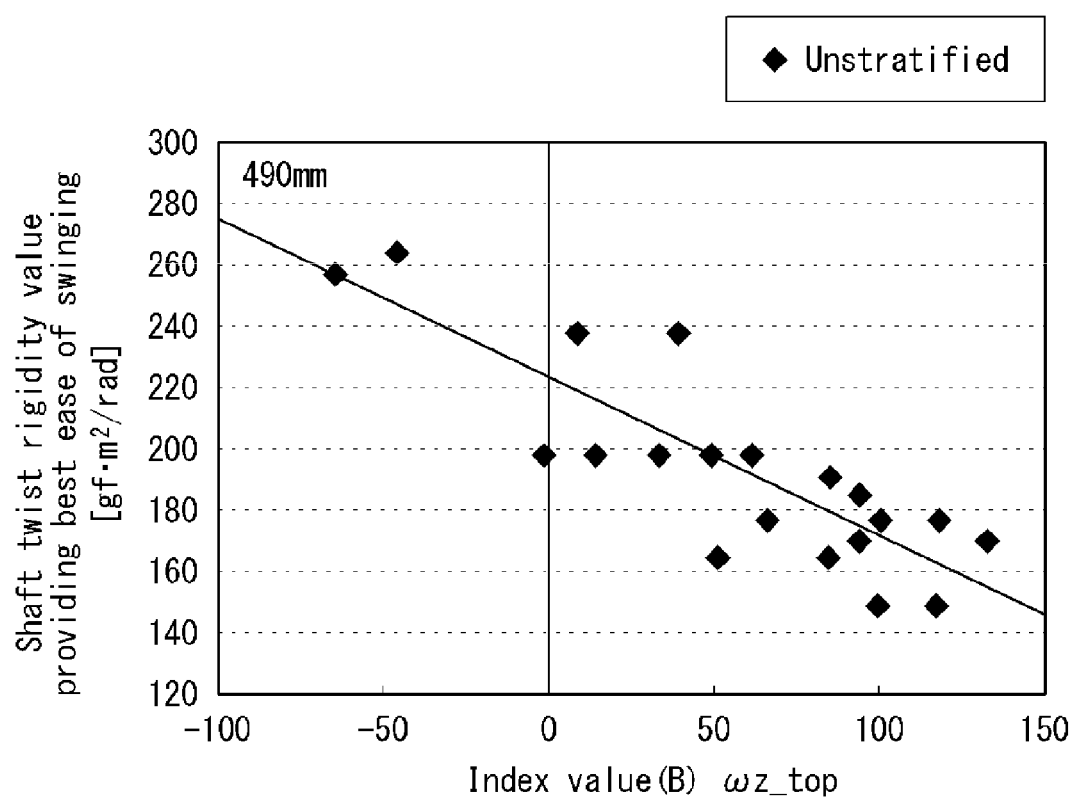
FIG. 29 shows an example of a relationship between the index value of the present invention and a shaft twist rigidity at the shaft middle part (490 mm) providing ease of swinging, and contains unstratified data.
Figure 30:
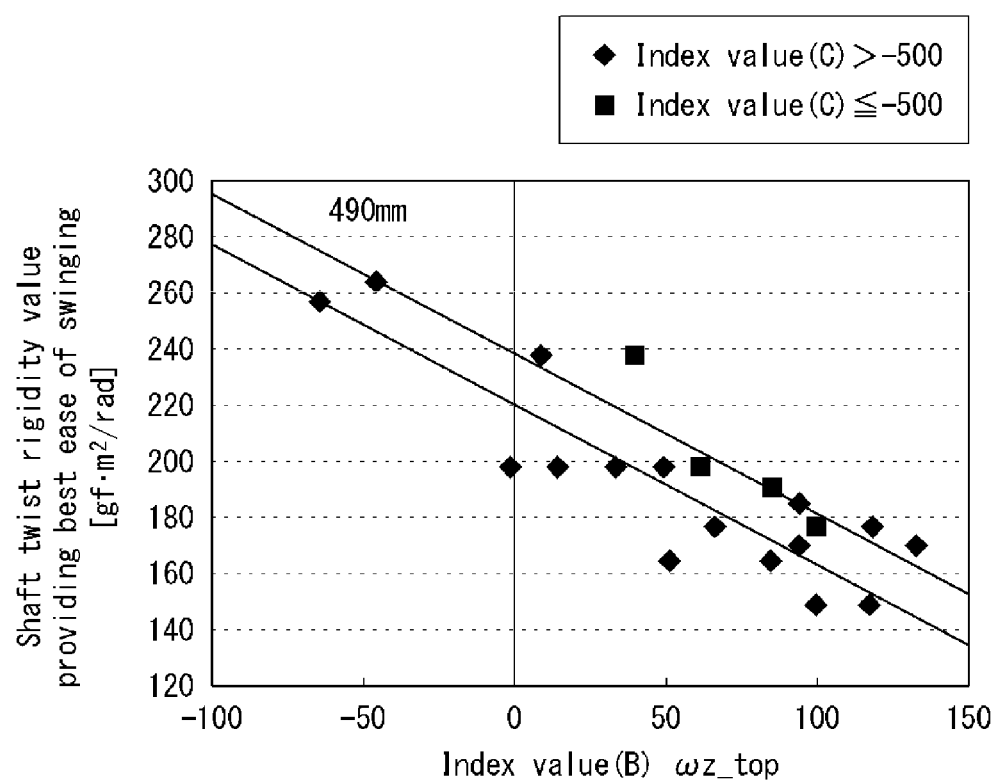
FIG. 30 shows an example of a relationship between the index value of the present invention and a shaft twist rigidity at the shaft middle part (490 mm) providing ease of swinging, and contains stratified data.
Figure 31:
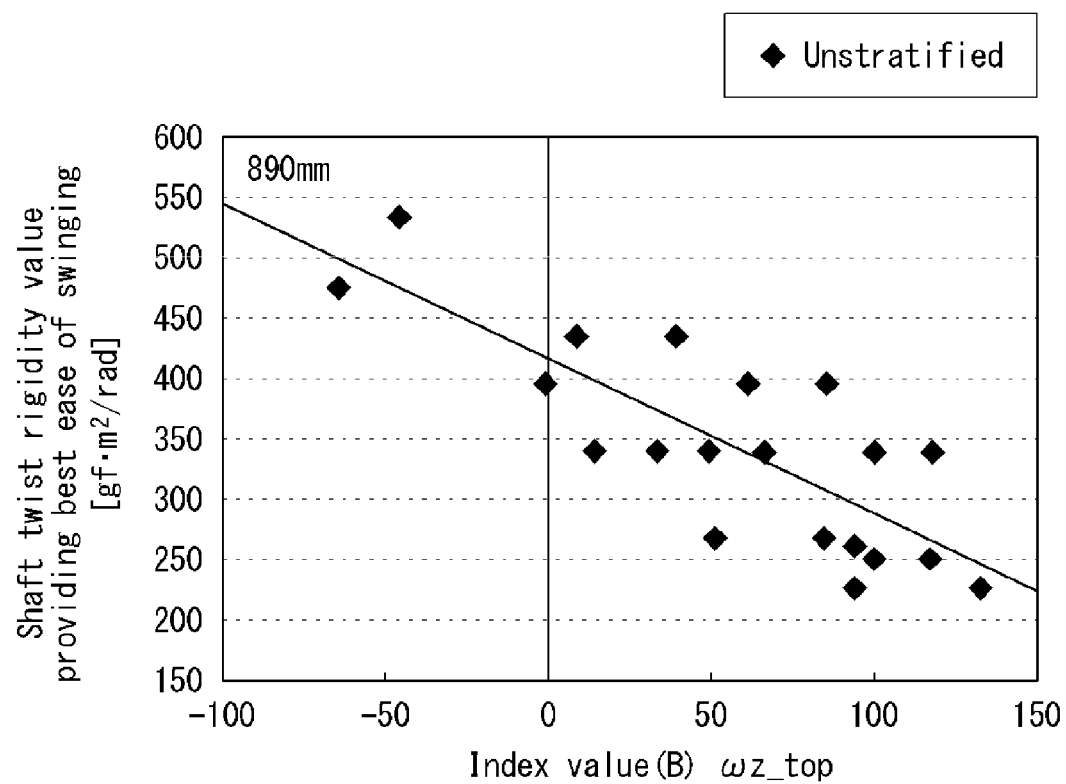
FIG. 31 shows an example of a relationship between the index value of the present invention and a shaft twist rigidity at the shaft back end part (890 mm) providing ease of swinging, and contains unstratified data.
Figure 32:
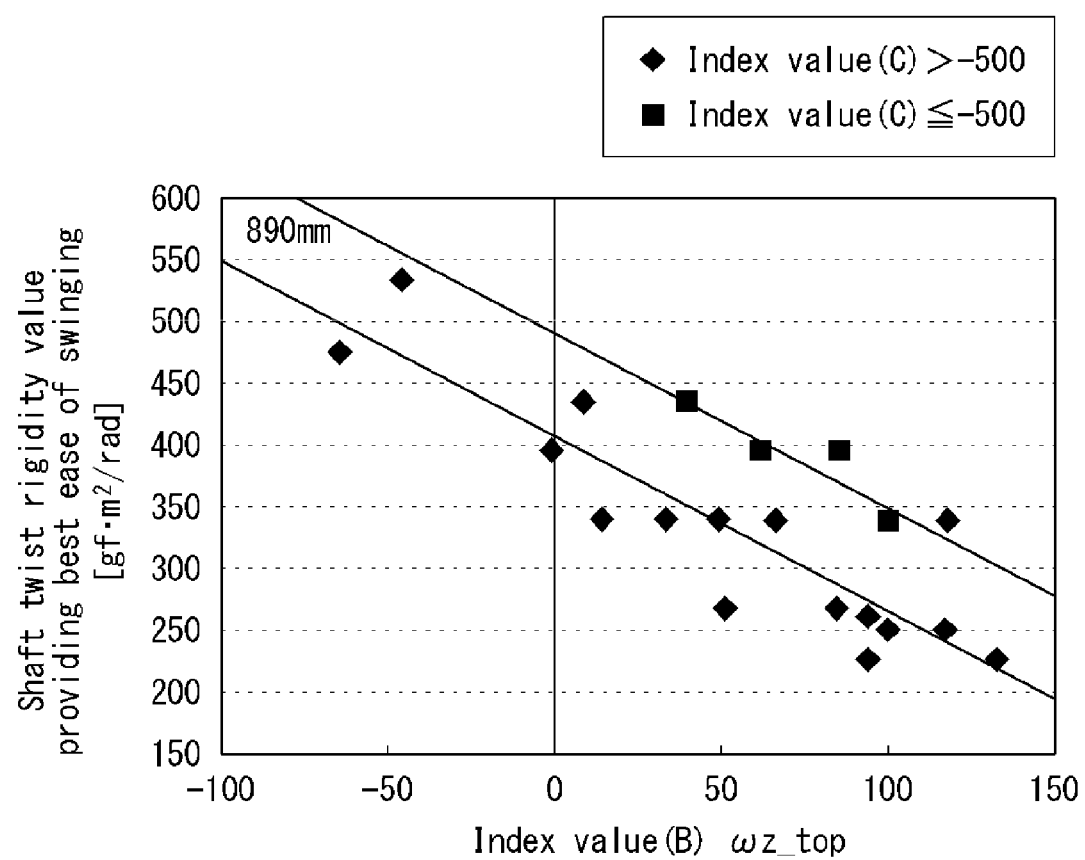
FIG. 32 shows an example of a relationship between the index value of the present invention and a shaft twist rigidity at the shaft back end part (890 mm) providing ease of swinging, and contains stratified data.

Furthermore, FIGS. 27, 29, and 31 corresponding to Table 11 show examples of the relationship between the index value (B) and the shaft twist rigidity at the shaft front end part (90 mm), the shaft middle part (490 mm), and the shaft back end part (890 mm), respectively, providing ease of swinging, and contain unstratified data. On the other hand, FIGS. 28, 30, and 32 corresponding to Table 12 show examples of the relationship between the index value (B) and the shaft twist rigidity at the shaft front end part (90 mm), the shaft middle part (490 mm), and the shaft back end part (890 mm), respectively, providing ease of swinging, and contain data stratified using the index value (C).

TABLE 9

| Tester | Flex | Shaft twist rigidity providing finest directionality | | | Index value (A) $\omega x\_(\omega y\_max\sim imp)/$ $t\_(\omega y\_max\sim imp)$ | Index value (B) $\omega z\_top$ |
|---|---|---|---|---|---|---|
| | | 90 mm | 490 mm | 890 mm | | |
| A | X | 72.4 | 265.5 | 537.6 | 40008.0 | 8.8 |
| B | X | 72.4 | 258.4 | 477.8 | 28774.2 | −45.8 |
| C | X | 72.4 | 265.5 | 537.6 | 42052.4 | 39.1 |
| D | X | 70.5 | 238.9 | 438.0 | 30005.6 | 85.1 |
| E | X | 70.5 | 238.9 | 438.0 | 25271.3 | −64.2 |
| F | S | 72.4 | 198.9 | 398.2 | 27499.6 | −1.2 |
| G | S | 66.4 | 199.1 | 341.3 | 29293.9 | 61.3 |
| H | S | 61.3 | 165.0 | 268.8 | 25570.2 | 51.1 |
| I | S | 72.4 | 198.9 | 398.2 | 34502.8 | 100.0 |
| J | S | 72.4 | 198.9 | 398.2 | 20856.1 | 49.2 |
| K | S | 56.9 | 177.2 | 341.3 | 20770.2 | 66.2 |
| L | S | 56.9 | 149.3 | 252.2 | 22593.5 | 117.0 |
| M | S | 56.9 | 149.3 | 252.2 | 22593.5 | 118.0 |
| N | S | 66.4 | 199.1 | 341.3 | 20315.1 | 14.2 |
| O | S | 66.4 | 199.1 | 341.3 | 23287.4 | 99.6 |
| P | R | 61.3 | 165.0 | 268.8 | 20023.1 | 94.0 |
| Q | R | 61.3 | 170.7 | 228.1 | 20697.1 | 94.0 |
| R | R | 61.3 | 165.0 | 268.8 | 17245.6 | 84.6 |
| S | R | 49.8 | 137.5 | 230.3 | 14793.0 | 33.5 |
| T | R | 49.8 | 137.5 | 230.3 | 16087.4 | 132.5 |

TABLE 10

| Tester | Flex | Shaft twist rigidity providing finest directionality | | | Index value (A) $\omega x\_(\omega y\_max\sim imp)/$ $t\_(\omega y\_max\sim imp)$ | Index value (B) $\omega z\_top$ |
|---|---|---|---|---|---|---|
| | | 90 mm | 490 mm | 890 mm | | |
| C | X | 72.4 | 265.5 | 537.6 | 42052.4 | 39.1 |
| D | X | 70.5 | 238.9 | 438.0 | 30005.6 | 85.1 |
| G | S | 66.4 | 199.1 | 341.3 | 29293.9 | 61.3 |
| H | S | 61.3 | 165.0 | 268.8 | 25570.2 | 51.1 |
| I | S | 72.4 | 198.9 | 398.2 | 34502.8 | 100.0 |
| J | S | 72.4 | 198.9 | 398.2 | 20856.1 | 49.2 |
| K | S | 56.9 | 177.2 | 341.3 | 20770.2 | 66.2 |
| L | S | 56.9 | 149.3 | 252.2 | 22593.5 | 117.0 |
| M | S | 56.9 | 149.3 | 252.2 | 22593.5 | 118.0 |
| O | S | 66.4 | 199.1 | 341.3 | 23287.4 | 99.6 |
| P | R | 61.3 | 165.0 | 268.8 | 20023.1 | 94.0 |
| Q | R | 61.3 | 170.7 | 228.1 | 20697.1 | 94.0 |
| R | R | 61.3 | 165.0 | 268.8 | 17245.6 | 84.6 |
| S | R | 49.8 | 137.5 | 230.3 | 14793.0 | 33.5 |

TABLE 10-continued

| Tester | Flex | Shaft twist rigidity providing finest directionality | | | Index value (A) ωx_(ωy_max~imp)/ t_(ωy_max~imp) | Index value (B) ωz_top |
| --- | --- | --- | --- | --- | --- | --- |
| | | 90 mm | 490 mm | 890 mm | | |
| T | R | 49.8 | 137.5 | 230.3 | 16087.4 | 132.5 |
| A | X | 72.4 | 265.5 | 537.6 | 40008.0 | 8.8 |
| B | X | 72.4 | 258.4 | 477.8 | 28774.2 | −45.8 |
| E | X | 70.5 | 238.9 | 438.0 | 25271.3 | −64.2 |
| F | S | 72.4 | 198.9 | 398.2 | 27499.6 | −1.2 |
| N | S | 66.4 | 199.1 | 341.3 | 20315.1 | 14.2 |

TABLE 11

| Tester | Flex | Shaft twist rigidity providing best ease of swinging | | | Index value (B) ωz_top | Index value (C) ωz_top~ωy_max/ t_top~ωy_max |
| --- | --- | --- | --- | --- | --- | --- |
| | | 90 mm | 490 mm | 890 mm | | |
| A | X | 70.5 | 238.9 | 438.0 | 8.8 | −447.4 |
| B | X | 72.4 | 265.5 | 537.6 | −45.8 | 10.1 |
| C | X | 70.5 | 238.9 | 438.0 | 39.1 | −609.1 |
| D | X | 66.2 | 191.4 | 398.2 | 85.1 | −909.8 |
| E | X | 72.4 | 258.4 | 477.8 | −64.2 | −71.0 |
| F | S | 72.4 | 198.9 | 398.2 | −1.2 | −354.9 |
| G | S | 72.4 | 198.9 | 398.2 | 61.3 | −591.3 |
| H | S | 61.3 | 165.0 | 268.8 | 51.1 | −364.0 |
| I | S | 56.9 | 177.2 | 341.3 | 100.0 | −571.0 |
| J | S | 66.4 | 199.1 | 341.3 | 49.2 | 120.0 |
| K | S | 56.9 | 177.2 | 341.3 | 66.2 | −338.7 |
| L | S | 56.9 | 149.3 | 252.2 | 117.0 | −298.3 |
| M | S | 56.9 | 177.2 | 341.3 | 118.0 | −245.0 |
| N | S | 66.4 | 199.1 | 341.3 | 14.2 | −275.2 |
| O | S | 56.9 | 149.3 | 252.2 | 99.6 | −22.1 |
| P | R | 60.2 | 185.6 | 262.4 | 94.0 | 186.1 |
| Q | R | 61.3 | 170.7 | 228.1 | 94.0 | 243.6 |
| R | R | 61.3 | 165.0 | 268.8 | 84.6 | −432.2 |
| S | R | 66.4 | 199.1 | 341.3 | 33.5 | −488.4 |
| T | R | 61.3 | 170.7 | 228.1 | 132.5 | −90.5 |

TABLE 12

| Tester | Flex | Shaft twist rigidity providing best ease of swinging | | | Index value (B) ωz_top | Index value (C) ωz_top~ωy_max/ t_top~ωy_max |
| --- | --- | --- | --- | --- | --- | --- |
| | | 90 mm | 490 mm | 890 mm | | |
| A | X | 70.5 | 238.9 | 438.0 | 8.8 | −447.4 |
| B | X | 72.4 | 265.5 | 537.6 | −45.8 | 10.1 |
| E | X | 72.4 | 258.4 | 477.8 | −64.2 | −71.0 |
| F | S | 72.4 | 198.9 | 398.2 | −1.2 | −354.9 |
| H | S | 61.3 | 165.0 | 268.8 | 51.1 | −364.0 |
| J | S | 66.4 | 199.1 | 341.3 | 49.2 | 120.0 |
| K | S | 56.9 | 177.2 | 341.3 | 66.2 | −338.7 |
| L | S | 56.9 | 149.3 | 252.2 | 117.0 | −298.3 |
| M | S | 56.9 | 177.2 | 341.3 | 118.0 | −245.0 |
| N | S | 66.4 | 199.1 | 341.3 | 14.2 | −275.2 |
| O | S | 56.9 | 149.3 | 252.2 | 99.6 | −22.1 |
| P | R | 60.2 | 185.6 | 262.4 | 94.0 | 186.1 |
| Q | R | 61.3 | 170.7 | 228.1 | 94.0 | 243.6 |
| R | R | 61.3 | 165.0 | 268.8 | 84.6 | −432.2 |
| S | R | 66.4 | 199.1 | 341.3 | 33.5 | −488.4 |
| T | R | 61.3 | 170.7 | 228.1 | 132.5 | −90.5 |
| C | X | 70.5 | 238.9 | 438.0 | 39.1 | −609.1 |
| D | X | 66.2 | 191.4 | 398.2 | 85.1 | −909.8 |
| G | S | 72.4 | 198.9 | 398.2 | 61.3 | −591.3 |
| I | S | 56.9 | 177.2 | 341.3 | 100.0 | −571.0 |

[Fitting Method]

When fitting is to be performed focusing on fine directionality of a hit ball, a twist rigidity value suitable for a golfer hoping for the fitting is calculated at three parts (front end part, middle part, and back end part) of the shaft, using the index value obtained from an actual swing by the golfer and formulae (7) to (9) or formulae (10) to (15). Next, from among multiple shafts, a shaft having twist rigidities that are closest to the three twist rigidity values is selected. With regard to the multiple shafts, the twist rigidity values at the three parts are measured in advance and stored in a database. For example, a shaft that provides the smallest sum of differences between a calculated twist rigidity value and a twist rigidity value stored in the database for each of the parts can be selected as a shaft matching the golfer. Fitting can be performed similarly also when focusing on the ease of swinging

REFERENCE SIGNS LIST 1 golf club
2 sensor
10 computer
11 shaft
B ball
G golfer.

The invention claimed is:

1. A fitting method, of a shaft of a golf club, for selecting a shaft having a torque matching a golfer based on a swing of the golfer, the method including the steps of:
   obtaining measurement values from a sensor attached to a grip of the golf club and capable of measuring angular velocities about three axes when a golf ball is hit by the golf club;
   obtaining a predetermined index value for the angular velocities quantified from the measurement values; and
   selecting a shaft matching the golfer from among multiple shafts whose torques have been measured in advance, based on a relationship established through test-hitting performed in advance between the index value and a torque of a shaft,
   wherein, when x-axis is oriented in a direction along toe-heel direction of a golf club head, when y-axis is oriented in a direction in which a ball is hit, and when z-axis is oriented to match an axial direction of a shaft, the fitting method further includes the steps of:
   determining address, top, and impact of a swing from the measurement values;
   calculating $t\_{\omega y\_max-imp}$, which is a time from when a grip angular velocity about the y-axis becomes maximum during a downswing to when the impact occurs;
   calculating $\omega x\_{\omega y\_max-}$, which is an average value of a grip angular velocity about the x-axis from when the grip angular velocity about the y-axis becomes maximum to when the impact occurs;
   calculating, as the index value, a magnitude of a change amount of the grip angular velocity about the x-axis per unit of time by dividing the calculated $\omega x\_{\omega y\_max-imp}$ by $t\_{\omega y\_max-imp}$; and
   calculating the torque of the shaft from the calculated magnitude of the change amount of the grip angular velocity about the x-axis per unit of time, using an approximate formula that is prepared in advance through test-hitting and that expresses a relationship between a torque of the shaft and the magnitude of the change amount of the grip angular velocity about the x-axis.

2. The fitting method of claim 1, wherein the sensor is attached to a grip end.

3. The fitting method of claim 1, wherein, as the approximate formula used for calculating the torque, one formula among multiple approximate formulae prepared in accordance with a magnitude of $\omega z_{\_top}$ which is a change amount of a grip angular velocity about the z-axis around the top is used.

4. The fitting method of claim 3, wherein, among the multiple approximate formulae, a first approximate formula is used when $\omega z_{\_top}$ is not lower than 20 (deg/s), and a second approximate formula is used when $\omega z_{13\ top}$ is lower than 20 (deg/s).

5. The fitting method of claim 1, wherein the fitting method further includes the steps of:
 calculating, as the index value, $\omega z_{\_top}$, which is a change amount of a grip angular velocity about the z-axis around the top; and
 calculating the torque of the shaft from the calculated change amount of the grip angular velocity about the z-axis, using an approximate formula that is prepared in advance through test-hitting and that expresses a relationship between a torque of the shaft and the change amount of the grip angular velocity about the z-axis.

6. The fitting method of claim 5, wherein, as the approximate formula used for calculating the torque, one formula among multiple approximate formulae prepared in accordance with a magnitude of the change amount of the grip angular velocity about the z-axis from when the top is reached to when a grip angular velocity about the y-axis becomes maximum during a downswing is used; and
 wherein a magnitude of the change amount of the grip angular velocity about the z-axis is a value obtained by dividing $\omega z_{\_top-\omega y\_max}$, which is an average value of the grip angular velocity about the z-axis from when the top is reached to when the grip angular velocity about the y-axis becomes maximum during the downswing, by $t_{\_top-\omega y\_max}$, which is a time from when the top is reached to when the grip angular velocity about the y-axis becomes maximum during the downswing.

7. The fitting method of claim 6, wherein, among the multiple approximate formulae, a third approximate formula is used when $\omega z_{\_top-\omega y\_max} / t_{\_top-\omega y\_max}$, which is a value obtained from the dividing, is not higher than $-500$ (deg/s$^2$), and a fourth approximate formula is used when $\omega z_{\_top-\omega y\_max}/t_{\_top-\omega y\_max}$ is higher than $-500$ (deg/s$^2$).

\* \* \* \* \*